United States Patent
Hale et al.

(10) Patent No.: US 7,987,846 B2
(45) Date of Patent: *Aug. 2, 2011

(54) METHOD AND APPARATUS FOR VAPORIZING A COMPOUND

(75) Inventors: Ron L. Hale, Sandia Park, NM (US); Soonho Song, Hillsborough, CA (US); Reynaldo J. Quintana, Redwood City, CA (US); Joshua D. Rabinowitz, Princeton, NJ (US); Alejandro C. Zaffaroni, Atherton, CA (US)

(73) Assignee: Alexza Pharmaceuticals, Inc., Mountain View, CA (US)

( * ) Notice: Subject to any disclaimer, the term of this patent is extended or adjusted under 35 U.S.C. 154(b) by 270 days.

This patent is subject to a terminal disclaimer.

(21) Appl. No.: 12/275,836

(22) Filed: Nov. 21, 2008

(65) Prior Publication Data
US 2009/0071477 A1 Mar. 19, 2009

Related U.S. Application Data

(63) Continuation of application No. 10/146,086, filed on May 13, 2002, now Pat. No. 7,458,374.

(51) Int. Cl.
*A61M 11/00* (2006.01)
(52) U.S. Cl. .......... 128/203.26; 128/203.27; 128/204.17
(58) Field of Classification Search .......... 128/203.17, 128/203.26, 203.27, 204.17, 202.21; 122/27, 122/28; 392/386, 387, 393; 431/357, 361, 431/362, 365; 126/263.01, 269, 261
See application file for complete search history.

(56) References Cited

U.S. PATENT DOCUMENTS

| | | | |
|---|---|---|---|
| 1,239,634 A | 9/1917 | Stuart |
| 1,535,486 A | 4/1925 | Lundy |
| 1,803,334 A | 5/1931 | Lehmann |
| 1,864,980 A | 6/1932 | Curran |
| 2,084,299 A | 6/1937 | Borden |
| 2,086,140 A | 7/1937 | Silten |
| 2,230,753 A | 2/1941 | Klavehn et al. |
| 2,230,754 A | 2/1941 | Klavehn et al. |
| 2,243,669 A | 5/1941 | Clyne |
| 2,309,846 A | 2/1943 | Holm |
| 2,469,656 A | 5/1949 | Lienert |
| 2,714,649 A | 8/1955 | Critzer |
| 2,741,812 A | 4/1956 | Andre |
| 2,761,055 A | 8/1956 | Ike |
| 2,887,106 A | 5/1959 | Robinson |
| 2,898,649 A | 8/1959 | Murray |

(Continued)

FOREIGN PATENT DOCUMENTS

CA 2152684 1/1996
(Continued)

OTHER PUBLICATIONS

U.S. Appl. No. 11/687,466, filed Mar. 16, 2007, Zaffaroni et al.
(Continued)

*Primary Examiner* — Steven O Douglas
(74) *Attorney, Agent, or Firm* — Swanson & Bratschun, L.L.C.

(57) ABSTRACT

Disclosed is a method and device for rapid heating of a substance. One embodiment includes a substance including a drug to be vaporized for inhalation therapy. A sealed fuel cell containing a combustible filament is placed in a heat exchange relationship with the substance. An igniter is operatively associated with the combustible element. The substance may be vaporized inside of a housing to allow the vaporized drug to aerosolize and be inhaled by a user.

12 Claims, 5 Drawing Sheets

U.S. PATENT DOCUMENTS

| | | |
|---|---|---|
| 2,902,484 A | 9/1959 | Horclois |
| 3,043,977 A | 7/1962 | Morowitz |
| 3,080,624 A | 3/1963 | Webber, III |
| 3,164,600 A | 1/1965 | Janssen et al. |
| 3,169,095 A | 2/1965 | Thiel et al. |
| 3,200,819 A | 8/1965 | Gilbert |
| 3,219,533 A | 11/1965 | Mullins |
| 3,282,729 A | 11/1966 | Richardson et al. |
| 3,296,249 A | 1/1967 | Bell |
| 3,299,185 A | 1/1967 | Oda et al. |
| 3,371,085 A | 2/1968 | Reeder et al. |
| 3,393,197 A | 7/1968 | Pachter |
| 3,433,791 A | 3/1969 | Bentley et al. |
| 3,560,607 A | 2/1971 | Hartley et al. |
| 3,701,782 A | 10/1972 | Hester |
| 3,749,547 A | 7/1973 | Gregory et al. |
| 3,763,347 A | 10/1973 | Whitaker et al. |
| 3,773,995 A | 11/1973 | Pachter et al. |
| 3,831,606 A | 8/1974 | Damani |
| 3,847,650 A | 11/1974 | Gregory et al. |
| 3,864,326 A | 2/1975 | Babington |
| 3,894,040 A | 7/1975 | Buzby, Jr. |
| 3,909,463 A | 9/1975 | Hartman |
| 3,930,796 A | 1/1976 | Haensel |
| 3,943,941 A | 3/1976 | Boyd et al. |
| 3,949,743 A | 4/1976 | Shanbrom |
| 3,971,377 A | 7/1976 | Damani |
| 3,982,095 A | 9/1976 | Robinson |
| 3,987,052 A | 10/1976 | Hester, Jr. |
| 4,008,723 A | 2/1977 | Borthwick et al. |
| 4,020,379 A | 4/1977 | Manning |
| 4,045,156 A | 8/1977 | Chu et al. |
| 4,079,742 A | 3/1978 | Rainer et al. |
| 4,104,210 A | 8/1978 | Coran et al. |
| 4,121,583 A | 10/1978 | Chen |
| 4,141,369 A | 2/1979 | Burruss |
| 4,160,765 A | 7/1979 | Weinstock |
| 4,166,087 A | 8/1979 | Cline et al. |
| 4,183,912 A | 1/1980 | Rosenthale |
| 4,184,099 A | 1/1980 | Lindauer et al. |
| 4,190,654 A | 2/1980 | Gherardi et al. |
| 4,198,200 A | 4/1980 | Fonda et al. |
| RE30,285 E | 5/1980 | Babington |
| 4,219,031 A | 8/1980 | Rainer et al. |
| 4,229,447 A | 10/1980 | Porter |
| 4,229,931 A | 10/1980 | Schlueter et al. |
| 4,232,002 A | 11/1980 | Nogrady |
| 4,236,544 A | 12/1980 | Osaka |
| 4,251,525 A | 2/1981 | Weinstock |
| 4,276,243 A | 6/1981 | Partus |
| 4,280,629 A | 7/1981 | Slaughter |
| 4,284,089 A | 8/1981 | Ray |
| 4,286,604 A | 9/1981 | Ehretsmann et al. |
| 4,303,083 A | 12/1981 | Burruss, Jr. |
| 4,340,072 A | 7/1982 | Bolt et al. |
| 4,346,059 A | 8/1982 | Spector |
| 4,347,855 A | 9/1982 | Lanzillotti et al. |
| 4,376,767 A | 3/1983 | Sloan |
| 4,391,285 A | 7/1983 | Burnett et al. |
| 4,423,071 A | 12/1983 | Chignac et al. |
| 4,474,191 A | 10/1984 | Steiner |
| 4,484,576 A | 11/1984 | Albarda |
| 4,508,726 A | 4/1985 | Coleman |
| 4,523,589 A | 6/1985 | Krauser |
| 4,556,539 A | 12/1985 | Spector |
| 4,566,451 A | 1/1986 | Badewien |
| 4,588,425 A | 5/1986 | Usry et al. |
| 4,588,721 A | 5/1986 | Mahan |
| 4,591,615 A | 5/1986 | Aldred et al. |
| 4,605,552 A | 8/1986 | Fritschi |
| 4,627,963 A | 12/1986 | Olson |
| 4,647,428 A | 3/1987 | Gyulay |
| 4,647,433 A | 3/1987 | Spector |
| 4,654,370 A | 3/1987 | Marriott, III et al. |
| 4,683,231 A | 7/1987 | Glassman |
| 4,693,868 A | 9/1987 | Katsuda et al. |
| 4,708,151 A | 11/1987 | Shelar |
| 4,714,082 A | 12/1987 | Banerjee et al. |
| 4,722,334 A | 2/1988 | Blackmer et al. |
| 4,734,560 A | 3/1988 | Bowen |
| 4,735,217 A | 4/1988 | Gerth et al. |
| 4,735,358 A | 4/1988 | Morita et al. |
| 4,753,758 A | 6/1988 | Miller |
| 4,755,508 A | 7/1988 | Bock et al. |
| 4,756,318 A | 7/1988 | Clearman et al. |
| 4,765,347 A | 8/1988 | Sensabaugh, Jr. et al. |
| 4,771,795 A | 9/1988 | White et al. |
| 4,774,971 A | 10/1988 | Vieten |
| 4,793,365 A | 12/1988 | Sensabaugh, Jr. et al. |
| 4,793,366 A | 12/1988 | Hill |
| 4,800,903 A | 1/1989 | Ray et al. |
| 4,801,411 A | 1/1989 | Wellinghoff et al. |
| 4,814,161 A | 3/1989 | Jinks et al. |
| 4,819,665 A | 4/1989 | Roberts et al. |
| 4,848,374 A | 7/1989 | Chard et al. |
| 4,852,561 A | 8/1989 | Sperry |
| 4,853,517 A | 8/1989 | Bowen et al. |
| 4,854,331 A | 8/1989 | Banerjee et al. |
| 4,858,630 A | 8/1989 | Banerjee et al. |
| 4,863,720 A | 9/1989 | Burghart et al. |
| 4,881,541 A | 11/1989 | Eger et al. |
| 4,881,556 A | 11/1989 | Clearman et al. |
| 4,889,850 A | 12/1989 | Thornfeldt et al. |
| 4,892,109 A | 1/1990 | Strubel |
| 4,895,719 A | 1/1990 | Radhakrishnun et al. |
| 4,906,417 A | 3/1990 | Gentry |
| 4,911,157 A | 3/1990 | Miller |
| 4,917,119 A | 4/1990 | Potter et al. |
| 4,917,120 A | 4/1990 | Hill |
| 4,917,830 A | 4/1990 | Ortiz et al. |
| 4,922,901 A | 5/1990 | Brooks et al. |
| 4,924,883 A | 5/1990 | Perfetti et al. |
| 4,928,714 A | 5/1990 | Shannon |
| 4,935,624 A | 6/1990 | Henion et al. |
| 4,941,483 A | 7/1990 | Ridings et al. |
| 4,947,874 A | 8/1990 | Brooks et al. |
| 4,947,875 A | 8/1990 | Brooks et al. |
| 4,950,664 A | 8/1990 | Goldberg |
| 4,955,945 A | 9/1990 | Weick |
| 4,959,380 A | 9/1990 | Wilson |
| 4,963,289 A | 10/1990 | Ortiz et al. |
| 4,968,885 A | 11/1990 | Willoughby |
| 4,984,158 A | 1/1991 | Hillsman |
| 4,989,619 A | 2/1991 | Clearman et al. |
| 5,016,425 A | 5/1991 | Weick |
| 5,017,575 A | 5/1991 | Golwyn |
| 5,019,122 A | 5/1991 | Clearman et al. |
| 5,020,548 A | 6/1991 | Farrier et al. |
| 5,027,836 A | 7/1991 | Shannon et al. |
| 5,033,483 A | 7/1991 | Clearman et al. |
| 5,038,769 A | 8/1991 | Krauser |
| 5,042,509 A | 8/1991 | Banerjee et al. |
| 5,049,389 A | 9/1991 | Radhakrishnun |
| 5,060,666 A | 10/1991 | Clearman et al. |
| 5,060,667 A | 10/1991 | Strubel |
| 5,060,671 A | 10/1991 | Counts et al. |
| 5,067,499 A | 11/1991 | Banerjee et al. |
| 5,072,726 A | 12/1991 | Mazloomdoost et al. |
| 5,076,292 A | 12/1991 | Sensabaugh, Jr. et al. |
| 5,093,894 A | 3/1992 | Deevi et al. |
| 5,095,921 A | 3/1992 | Loose et al. |
| 5,099,861 A | 3/1992 | Clearman et al. |
| 5,105,831 A | 4/1992 | Banerjee et al. |
| 5,109,180 A | 4/1992 | Boultinghouse et al. |
| 5,112,598 A | 5/1992 | Biesalski |
| 5,118,494 A | 6/1992 | Schultz et al. |
| 5,119,834 A | 6/1992 | Shannon et al. |
| 5,126,123 A | 6/1992 | Johnson |
| 5,133,368 A | 7/1992 | Neumann et al. |
| 5,135,009 A | 8/1992 | Muller et al. |
| 5,137,034 A | 8/1992 | Perfetti et al. |
| 5,144,962 A | 9/1992 | Counts et al. |
| 5,146,915 A | 9/1992 | Montgomery |
| 5,149,538 A | 9/1992 | Granger et al. |
| 5,156,170 A | 10/1992 | Clearman et al. |
| 5,160,664 A | 11/1992 | Liu |
| 5,164,740 A | 11/1992 | Ivri |

| | | | | | |
|---|---|---|---|---|---|
| 5,166,202 A | 11/1992 | Schweizer | 5,694,919 A | 12/1997 | Rubsamen et al. |
| 5,167,242 A | 12/1992 | Turner et al. | 5,718,222 A | 2/1998 | Lloyd et al. |
| 5,177,071 A | 1/1993 | Freidinger et al. | 5,724,957 A | 3/1998 | Rubsamen et al. |
| 5,179,966 A | 1/1993 | Losee et al. | 5,725,756 A | 3/1998 | Subramaniam et al. |
| 5,186,164 A | 2/1993 | Raghuprasad | 5,733,572 A | 3/1998 | Unger et al. |
| 5,192,548 A | 3/1993 | Velasquez et al. | 5,735,263 A | 4/1998 | Rubsamen et al. |
| 5,224,498 A | 7/1993 | Deevi et al. | 5,738,865 A | 4/1998 | Baichwal et al. |
| 5,226,411 A | 7/1993 | Levine | 5,743,250 A | 4/1998 | Gonda et al. |
| 5,229,120 A | 7/1993 | DeVincent | 5,743,251 A | 4/1998 | Howell et al. |
| 5,229,382 A | 7/1993 | Chakrabarti et al. | 5,744,469 A | 4/1998 | Tran |
| 5,240,922 A | 8/1993 | O'Neill | 5,747,001 A | 5/1998 | Wiedmann et al. |
| 5,249,586 A | 10/1993 | Morgan et al. | 5,756,449 A | 5/1998 | Andersen et al. |
| 5,255,674 A | 10/1993 | Oftedal et al. | 5,758,637 A | 6/1998 | Ivri et al. |
| 5,261,424 A | 11/1993 | Sprinkel | 5,767,117 A | 6/1998 | Moskowitz et al. |
| 5,264,433 A | 11/1993 | Sato et al. | 5,769,621 A | 6/1998 | Early et al. |
| 5,269,327 A | 12/1993 | Counts et al. | 5,770,222 A | 6/1998 | Unger et al. |
| 5,284,133 A | 2/1994 | Burns et al. | 5,771,882 A | 6/1998 | Psaros et al. |
| 5,285,798 A | 2/1994 | Banerjee et al. | 5,776,928 A | 7/1998 | Beasley, Jr. |
| 5,292,499 A | 3/1994 | Evans et al. | 5,804,212 A | 9/1998 | Illum |
| 5,322,075 A | 6/1994 | Deevi et al. | 5,809,997 A | 9/1998 | Wolf |
| 5,333,106 A | 7/1994 | Lanpher et al. | 5,817,656 A | 10/1998 | Beasley, Jr. et al. |
| 5,345,951 A | 9/1994 | Serrano et al. | 5,819,756 A | 10/1998 | Mielordt |
| 5,357,984 A | 10/1994 | Farrier et al. | 5,823,178 A | 10/1998 | Lloyd et al. |
| 5,363,842 A | 11/1994 | Mishelevich et al. | 5,829,436 A | 11/1998 | Rubsamen et al. |
| 5,364,838 A | 11/1994 | Rubsamen | 5,833,891 A | 11/1998 | Subramaniam et al. |
| 5,366,770 A | 11/1994 | Wang | 5,840,246 A | 11/1998 | Hammons et al. |
| 5,372,148 A | 12/1994 | McCafferty et al. | 5,855,564 A | 1/1999 | Ruskewicz |
| 5,376,386 A | 12/1994 | Ganderton et al. | 5,855,913 A | 1/1999 | Hanes et al. |
| 5,388,574 A | 2/1995 | Ingebrethsen | 5,865,185 A | 2/1999 | Collins et al. |
| 5,391,081 A | 2/1995 | Lampotang et al. | 5,874,064 A | 2/1999 | Edwards et al. |
| 5,399,574 A | 3/1995 | Robertson et al. | 5,874,481 A | 2/1999 | Weers et al. |
| 5,400,808 A | 3/1995 | Turner et al. | 5,875,776 A | 3/1999 | Vaghefi |
| 5,400,969 A | 3/1995 | Keene | 5,878,752 A | 3/1999 | Adams et al. |
| 5,402,517 A | 3/1995 | Gillett et al. | 5,884,620 A | 3/1999 | Gonda et al. |
| 5,408,574 A | 4/1995 | Deevi et al. | 5,890,908 A | 4/1999 | Lampotang et al. |
| 5,436,230 A | 7/1995 | Soudant et al. | 5,894,841 A | 4/1999 | Voges |
| 5,451,408 A | 9/1995 | Mezei et al. | 5,904,900 A | 5/1999 | Bleuse et al. |
| 5,455,043 A | 10/1995 | Fischel-Ghodsian | 5,906,811 A | 5/1999 | Hersh |
| 5,456,247 A | 10/1995 | Shilling et al. | 5,907,075 A | 5/1999 | Subramaniam et al. |
| 5,456,677 A | 10/1995 | Spector | 5,910,301 A | 6/1999 | Farr et al. |
| 5,457,100 A | 10/1995 | Daniel | 5,915,378 A | 6/1999 | Lloyd et al. |
| 5,457,101 A | 10/1995 | Greenwood et al. | 5,918,595 A | 7/1999 | Olsson |
| 5,459,137 A | 10/1995 | Andrasi et al. | 5,928,520 A | 7/1999 | Haumesser |
| 5,462,740 A | 10/1995 | Evenstad et al. | 5,929,093 A | 7/1999 | Pang et al. |
| 5,468,936 A | 11/1995 | Deevi et al. | 5,934,272 A | 8/1999 | Lloyd et al. |
| 5,479,948 A | 1/1996 | Counts et al. | 5,934,289 A | 8/1999 | Watkins et al. |
| 5,501,236 A | 3/1996 | Hill et al. | 5,935,604 A | 8/1999 | Illum |
| 5,505,214 A | 4/1996 | Collins et al. | 5,938,117 A | 8/1999 | Ivri |
| 5,507,277 A | 4/1996 | Rubsamen et al. | 5,939,100 A | 8/1999 | Albrechtsen et al. |
| 5,511,726 A | 4/1996 | Greenspan et al. | 5,941,240 A | 8/1999 | Gonda et al. |
| 5,519,019 A | 5/1996 | Andrasi et al. | 5,944,012 A | 8/1999 | Pera |
| 5,525,329 A | 6/1996 | Snyder et al. | 5,957,124 A | 9/1999 | Lloyd et al. |
| 5,537,507 A | 7/1996 | Mariner et al. | 5,960,792 A | 10/1999 | Lloyd et al. |
| 5,538,020 A | 7/1996 | Farrier et al. | 5,970,973 A | 10/1999 | Gonda et al. |
| 5,540,959 A | 7/1996 | Wang | 5,971,951 A | 10/1999 | Ruskewicz |
| 5,543,434 A | 8/1996 | Weg | 5,985,309 A | 11/1999 | Edwards et al. |
| 5,544,646 A | 8/1996 | Lloyd et al. | 5,993,805 A | 11/1999 | Sutton et al. |
| 5,564,442 A | 10/1996 | MacDonald et al. | 6,004,516 A | 12/1999 | Rasouli et al. |
| 5,565,148 A | 10/1996 | Pendergrass | 6,004,970 A | 12/1999 | O'Malley et al. |
| 5,577,156 A | 11/1996 | Costello | 6,008,214 A | 12/1999 | Kwon et al. |
| 5,584,701 A | 12/1996 | Lampotang et al. | 6,008,216 A | 12/1999 | Chakrabarti et al. |
| 5,586,550 A | 12/1996 | Ivri et al. | 6,013,050 A | 1/2000 | Bellhouse et al. |
| 5,591,409 A | 1/1997 | Watkins | 6,014,969 A | 1/2000 | Lloyd et al. |
| 5,592,934 A | 1/1997 | Thwaites | 6,014,970 A | 1/2000 | Ivri et al. |
| 5,593,792 A | 1/1997 | Farrier et al. | 6,041,777 A | 3/2000 | Faithfull et al. |
| 5,605,146 A | 2/1997 | Sarela | 6,044,777 A | 4/2000 | Walsh |
| 5,605,897 A | 2/1997 | Beasley, Jr. et al. | 6,048,550 A | 4/2000 | Chan et al. |
| 5,607,691 A | 3/1997 | Hale et al. | 6,048,857 A | 4/2000 | Ellinwood, Jr. et al. |
| 5,613,504 A | 3/1997 | Collins et al. | 6,050,260 A | 4/2000 | Daniell et al. |
| 5,613,505 A | 3/1997 | Campbell et al. | 6,051,257 A | 4/2000 | Kodas et al. |
| 5,619,984 A | 4/1997 | Hodson et al. | 6,051,566 A | 4/2000 | Bianco |
| 5,622,944 A | 4/1997 | Hale et al. | 6,053,176 A | 4/2000 | Adams et al. |
| 5,627,178 A | 5/1997 | Chakrabarti et al. | RE36,744 E | 6/2000 | Goldberg |
| 5,649,554 A | 7/1997 | Sprinkel | 6,085,026 A | 7/2000 | Hammons et al. |
| 5,655,523 A | 8/1997 | Hodson et al. | 6,089,857 A | 7/2000 | Matsuura et al. |
| 5,656,255 A | 8/1997 | Jones | 6,090,212 A | 7/2000 | Mahawili |
| 5,660,166 A | 8/1997 | Lloyd et al. | 6,090,403 A | 7/2000 | Block et al. |
| 5,666,977 A | 9/1997 | Higgins et al. | 6,095,134 A | 8/2000 | Sievers et al. |
| 5,690,809 A | 11/1997 | Subramaniam et al. | 6,095,153 A | 8/2000 | Kessler et al. |

| | | | | | | |
|---|---|---|---|---|---|---|
| 6,098,620 | A | 8/2000 | Lloyd et al. | 6,783,753 B2 | 8/2004 | Rabinowitz et al. |
| 6,102,036 | A | 8/2000 | Slutsky et al. | 6,797,259 B2 | 9/2004 | Rabinowitz et al. |
| 6,113,795 | A | 9/2000 | Subramaniam et al. | 6,803,031 B2 | 10/2004 | Rabinowitz et al. |
| 6,117,866 | A | 9/2000 | Bondinell et al. | 6,805,853 B2 | 10/2004 | Rabinowitz et al. |
| 6,125,853 | A | 10/2000 | Susa et al. | 6,805,854 B2 | 10/2004 | Hale et al. |
| 6,126,919 | A | 10/2000 | Stefely et al. | 6,814,954 B2 | 11/2004 | Rabinowitz et al. |
| 6,131,566 | A | 10/2000 | Ashurst et al. | 6,814,955 B2 | 11/2004 | Rabinowitz et al. |
| 6,131,570 | A | 10/2000 | Schuster et al. | 6,855,310 B2 | 2/2005 | Rabinowitz et al. |
| 6,133,327 | A | 10/2000 | Kimura et al. | 6,884,408 B2 | 4/2005 | Rabinowitz et al. |
| 6,135,369 | A | 10/2000 | Prendergast et al. | 6,994,843 B2 | 2/2006 | Rabinowitz et al. |
| 6,136,295 | A | 10/2000 | Edwards et al. | 7,005,121 B2 | 2/2006 | Rabinowitz et al. |
| 6,138,683 | A | 10/2000 | Hersh et al. | 7,005,122 B2 | 2/2006 | Hale et al. |
| 6,140,323 | A | 10/2000 | Ellinwood, Jr. et al. | 7,008,615 B2 | 3/2006 | Rabinowitz et al. |
| 6,143,277 | A | 11/2000 | Ashurst et al. | 7,008,616 B2 | 3/2006 | Rabinowitz et al. |
| 6,143,746 | A | 11/2000 | Daugan et al. | 7,011,819 B2 | 3/2006 | Hale et al. |
| 6,149,892 | A | 11/2000 | Britto | 7,011,820 B2 | 3/2006 | Rabinowitz et al. |
| 6,155,268 | A | 12/2000 | Takeuchi | 7,014,840 B2 | 3/2006 | Hale et al. |
| 6,158,431 | A | 12/2000 | Poole | 7,014,841 B2 | 3/2006 | Rabinowitz et al. |
| 6,167,880 | B1 | 1/2001 | Gonda et al. | 7,018,619 B2 | 3/2006 | Rabinowitz et al. |
| 6,178,969 | B1 | 1/2001 | St. Charles | 7,018,620 B2 | 3/2006 | Rabinowitz et al. |
| 6,234,167 | B1 | 5/2001 | Cox et al. | 7,018,621 B2 | 3/2006 | Hale et al. |
| 6,241,969 | B1 | 6/2001 | Saidi et al. | 7,022,312 B2 | 4/2006 | Rabinowitz et al. |
| 6,250,301 | B1 | 6/2001 | Pate | 7,029,658 B2 | 4/2006 | Rabinowitz et al. |
| 6,255,334 | B1 | 7/2001 | Sands | 7,033,575 B2 | 4/2006 | Rabinowitz et al. |
| 6,263,872 | B1 | 7/2001 | Schuster et al. | 7,045,118 B2 | 5/2006 | Rabinowitz et al. |
| 6,264,922 | B1 | 7/2001 | Wood et al. | 7,045,119 B2 | 5/2006 | Rabinowitz et al. |
| 6,284,287 | B1 | 9/2001 | Sarlikiotis et al. | 7,048,909 B2 | 5/2006 | Rabinowitz et al. |
| 6,299,900 | B1 | 10/2001 | Reed et al. | 7,052,679 B2 | 5/2006 | Rabinowitz et al. |
| 6,300,710 | B1 | 10/2001 | Nakamori | 7,052,680 B2 | 5/2006 | Rabinowitz et al. |
| 6,306,431 | B1 | 10/2001 | Zhang et al. | 7,060,254 B2 | 6/2006 | Rabinowitz et al. |
| 6,309,668 | B1 | 10/2001 | Bastin et al. | 7,060,255 B2 | 6/2006 | Rabinowitz et al. |
| 6,309,986 | B1 | 10/2001 | Flashinski et al. | 7,063,830 B2 | 6/2006 | Rabinowitz et al. |
| 6,313,176 | B1 | 11/2001 | Ellinwood, Jr. et al. | 7,063,831 B2 | 6/2006 | Rabinowitz et al. |
| 6,325,475 | B1 | 12/2001 | Hayes et al. | 7,063,832 B2 | 6/2006 | Rabinowitz et al. |
| 6,390,453 | B1 | 5/2002 | Frederickson et al. | 7,067,114 B2 | 6/2006 | Rabinowitz et al. |
| 6,408,854 | B1 | 6/2002 | Gonda et al. | 7,070,761 B2 | 7/2006 | Rabinowitz et al. |
| 6,413,930 | B1 | 7/2002 | Ratti et al. | 7,070,762 B2 | 7/2006 | Rabinowitz et al. |
| 6,420,351 | B1 | 7/2002 | Tsai et al. | 7,070,763 B2 | 7/2006 | Rabinowitz et al. |
| 6,431,166 | B2 | 8/2002 | Gonda et al. | 7,070,764 B2 | 7/2006 | Rabinowitz et al. |
| 6,443,152 | B1 | 9/2002 | Lockhart et al. | 7,070,765 B2 | 7/2006 | Rabinowitz et al. |
| 6,461,591 | B1 | 10/2002 | Keller et al. | 7,070,766 B2 | 7/2006 | Rabinowitz et al. |
| 6,491,233 | B2 | 12/2002 | Nichols | 7,078,016 B2 | 7/2006 | Rabinowitz et al. |
| 6,501,052 | B2 | 12/2002 | Cox et al. | 7,078,017 B2 | 7/2006 | Rabinowitz et al. |
| 6,506,762 | B1 | 1/2003 | Horvath et al. | 7,078,018 B2 | 7/2006 | Rabinowitz et al. |
| 6,514,482 | B1 | 2/2003 | Bartus et al. | 7,078,019 B2 | 7/2006 | Rabinowitz et al. |
| 6,516,796 | B1 | 2/2003 | Cox et al. | 7,078,020 B2 | 7/2006 | Rabinowitz et al. |
| 6,557,552 | B1 | 5/2003 | Cox et al. | 7,087,216 B2 | 8/2006 | Rabinowitz et al. |
| 6,561,186 | B2 | 5/2003 | Casper et al. | 7,087,217 B2 | 8/2006 | Rabinowitz et al. |
| 6,568,390 | B2 | 5/2003 | Nichols et al. | 7,087,218 B2 | 8/2006 | Rabinowitz et al. |
| 6,591,839 | B2 | 7/2003 | Meyer et al. | 7,090,830 B2 | 8/2006 | Hale et al. |
| 6,632,047 | B2 | 10/2003 | Vinegar et al. | 7,094,392 B2 | 8/2006 | Rabinowitz et al. |
| 6,648,950 | B2 | 11/2003 | Lee et al. | 7,108,847 B2 | 9/2006 | Rabinowitz et al. |
| 6,671,945 | B2 | 1/2004 | Gerber et al. | 7,115,250 B2 | 10/2006 | Rabinowitz et al. |
| 6,680,668 | B2 | 1/2004 | Goldberger et al. | 7,169,378 B2 | 1/2007 | Rabinowitz et al. |
| 6,681,769 | B2 | 1/2004 | Sprinkel et al. | 7,402,777 B2 | 7/2008 | Hale et al. |
| 6,681,998 | B2 | 1/2004 | Sharpe et al. | 7,442,368 B2 | 10/2008 | Rabinowitz et al. |
| 6,682,716 | B2 | 1/2004 | Hodges et al. | 7,445,768 B2 | 11/2008 | Rabinowitz et al. |
| 6,688,313 | B2 | 2/2004 | Wrenn et al. | 7,449,172 B2 | 11/2008 | Rabinowitz et al. |
| 6,694,975 | B2 | 2/2004 | Schuster et al. | 7,449,173 B2 | 11/2008 | Rabinowitz et al. |
| 6,701,921 | B2 | 3/2004 | Sprinkel et al. | 7,449,174 B2 | 11/2008 | Rabinowitz et al. |
| 6,701,922 | B2 | 3/2004 | Hindle et al. | 7,449,175 B2 | 11/2008 | Rabinowitz et al. |
| 6,715,487 | B2 | 4/2004 | Nichols et al. | 7,458,374 B2 | 12/2008 | Hale et al. |
| 6,716,415 | B2 | 4/2004 | Rabinowitz et al. | 2001/0020147 A1 | 9/2001 | Staniforth et al. |
| 6,716,416 | B2 | 4/2004 | Rabinowitz et al. | 2001/0042546 A1 | 11/2001 | Umeda et al. |
| 6,716,417 | B2 | 4/2004 | Rabinowitz et al. | 2002/0031480 A1 | 3/2002 | Peart et al. |
| 6,728,478 | B2 | 4/2004 | Cox et al. | 2002/0037828 A1 | 3/2002 | Wilson et al. |
| 6,737,042 | B2 | 5/2004 | Rabinowitz et al. | 2002/0061281 A1 | 5/2002 | Osbakken et al. |
| 6,737,043 | B2 | 5/2004 | Rabinowitz et al. | 2002/0078955 A1 | 6/2002 | Nichols et al. |
| 6,740,307 | B2 | 5/2004 | Rabinowitz et al. | 2002/0086852 A1 | 7/2002 | Cantor |
| 6,740,308 | B2 | 5/2004 | Rabinowitz et al. | 2002/0097139 A1 | 7/2002 | Gerber et al. |
| 6,740,309 | B2 | 5/2004 | Rabinowitz et al. | 2002/0112723 A1 | 8/2002 | Schuster et al. |
| 6,743,415 | B2 | 6/2004 | Rabinowitz et al. | 2002/0117175 A1 | 8/2002 | Kottayil et al. |
| 6,759,029 | B2 | 7/2004 | Hale et al. | 2002/0176841 A1 | 11/2002 | Barker et al. |
| 6,772,756 | B2 | 8/2004 | Shayan | 2003/0004142 A1 | 1/2003 | Prior et al. |
| 6,772,757 | B2 | 8/2004 | Sprinkel, Jr. et al. | 2003/0015196 A1 | 1/2003 | Hodges et al. |
| 6,776,978 | B2 | 8/2004 | Rabinowitz et al. | 2003/0015197 A1 | 1/2003 | Hale et al. |
| 6,779,520 | B2 | 8/2004 | Genova et al. | 2003/0032638 A1 | 2/2003 | Kim et al. |
| 6,780,399 | B2 | 8/2004 | Rabinowitz et al. | 2003/0033055 A1 | 2/2003 | McRae et al. |
| 6,780,400 | B2 | 8/2004 | Rabinowitz et al. | 2003/0049025 A1 | 3/2003 | Neumann et al. |

| Publication No. | Date | Inventor |
|---|---|---|
| 2003/0051728 A1 | 3/2003 | Lloyd et al. |
| 2003/0062042 A1 | 4/2003 | Wensley et al. |
| 2003/0106551 A1 | 6/2003 | Sprinkel et al. |
| 2003/0118512 A1 | 6/2003 | Shen |
| 2003/0121906 A1 | 7/2003 | Abbott et al. |
| 2003/0131843 A1 | 7/2003 | Lu |
| 2003/0132219 A1 | 7/2003 | Cox et al. |
| 2003/0138508 A1 | 7/2003 | Novack et al. |
| 2003/0156829 A1 | 8/2003 | Cox et al. |
| 2004/0009128 A1 | 1/2004 | Rabinowitz et al. |
| 2004/0016427 A1 | 1/2004 | Byron et al. |
| 2004/0035409 A1 | 2/2004 | Harwig et al. |
| 2004/0055504 A1 | 3/2004 | Lee et al. |
| 2004/0081624 A1 | 4/2004 | Nguyen et al. |
| 2004/0096402 A1 | 5/2004 | Hodges et al. |
| 2004/0099266 A1 | 5/2004 | Cross et al. |
| 2004/0101481 A1 | 5/2004 | Hale et al. |
| 2004/0102434 A1 | 5/2004 | Hale et al. |
| 2004/0105818 A1 | 6/2004 | Every et al. |
| 2004/0105819 A1 | 6/2004 | Hale et al. |
| 2004/0234699 A1 | 11/2004 | Hale et al. |
| 2004/0234914 A1 | 11/2004 | Hale et al. |
| 2004/0234916 A1 | 11/2004 | Hale et al. |
| 2005/0034723 A1 | 2/2005 | Bennett et al. |
| 2005/0037506 A1 | 2/2005 | Hale et al. |
| 2005/0079166 A1 | 4/2005 | Damani et al. |
| 2005/0126562 A1 | 6/2005 | Rabinowitz et al. |
| 2005/0131739 A1 | 6/2005 | Rabinowitz et al. |
| 2005/0268911 A1 | 12/2005 | Cross et al. |
| 2006/0032496 A1 | 2/2006 | Hale et al. |
| 2006/0032501 A1 | 2/2006 | Hale et al. |
| 2006/0120962 A1 | 6/2006 | Rabinowitz et al. |
| 2006/0193788 A1 | 8/2006 | Hale et al. |
| 2006/0216243 A1 | 9/2006 | Rabinowitz et al. |
| 2006/0216244 A1 | 9/2006 | Rabinowitz et al. |
| 2006/0233717 A1 | 10/2006 | Hale et al. |
| 2006/0233719 A1 | 10/2006 | Rabinowitz et al. |
| 2006/0239936 A1 | 10/2006 | Rabinowitz et al. |
| 2006/0246011 A1 | 11/2006 | Rabinowitz et al. |
| 2006/0246012 A1 | 11/2006 | Rabinowitz et al. |
| 2006/0257328 A1 | 11/2006 | Rabinowitz et al. |
| 2006/0257329 A1 | 11/2006 | Rabinowitz et al. |
| 2006/0269486 A1 | 11/2006 | Rabinowitz et al. |
| 2006/0269487 A1 | 11/2006 | Rabinowitz et al. |
| 2006/0280692 A1 | 12/2006 | Rabinowitz et al. |
| 2006/0286043 A1 | 12/2006 | Rabinowitz et al. |
| 2007/0014737 A1 | 1/2007 | Rabinowitz et al. |
| 2007/0028916 A1 | 2/2007 | Hale et al. |
| 2007/0031340 A1 | 2/2007 | Hale et al. |
| 2007/0122353 A1 | 5/2007 | Hale et al. |
| 2007/0140982 A1 | 6/2007 | Every et al. |
| 2007/0178052 A1 | 8/2007 | Rabinowitz et al. |
| 2007/0286816 A1 | 12/2007 | Hale et al. |
| 2008/0110872 A1 | 5/2008 | Hale et al. |
| 2008/0175796 A1 | 7/2008 | Rabinowitz et al. |
| 2008/0216828 A1 | 9/2008 | Wensley |

FOREIGN PATENT DOCUMENTS

| | | |
|---|---|---|
| CN | 1082365 | 2/1994 |
| CN | 1176075 | 3/1998 |
| DE | 198 54 007 | 5/2000 |
| DE | 198 54 009 | 5/2000 |
| EP | 0 039 369 | 11/1981 |
| EP | 0 264 195 | 4/1988 |
| EP | 0 277 519 | 8/1988 |
| EP | 0 358 114 | 3/1990 |
| EP | 0 430 559 | 6/1991 |
| EP | 0 430 566 | 6/1991 |
| EP | 0 492 485 | 7/1992 |
| EP | 0 532 194 | 3/1993 |
| EP | 0 606 486 | 7/1994 |
| EP | 0 734 719 | 2/1996 |
| EP | 0 967 214 | 12/1999 |
| EP | 1 080 720 | 3/2001 |
| EP | 1 177 793 | 2/2002 |
| EP | 0 808 635 B1 | 7/2003 |
| FR | 921 852 A | 5/1947 |
| FR | 2 428 068 A | 1/1980 |
| GB | 502 761 | 1/1938 |
| GB | 903 866 | 8/1962 |
| GB | 1 366 041 | 9/1974 |
| GB | 2 108 390 | 5/1983 |
| GB | 2 122 903 | 1/1984 |
| HU | 200105 B | 10/1988 |
| HU | 219392 B | 6/1993 |
| JP | S56-87036 | 6/1988 |
| WO | WO 85/00520 | 2/1985 |
| WO | WO 88/08304 | 11/1988 |
| WO | WO 90/02737 | 3/1990 |
| WO | WO 90/07333 | 7/1990 |
| WO | WO 91/07947 | 6/1991 |
| WO | WO 91/18525 | 12/1991 |
| WO | WO 92/05781 | 4/1992 |
| WO | WO 92/15353 | 9/1992 |
| WO | WO 92/19303 | 11/1992 |
| WO | WO 93/12823 | 7/1993 |
| WO | WO 94/09842 | 5/1994 |
| WO | WO 94/16717 | 8/1994 |
| WO | WO 94/16757 | 8/1994 |
| WO | WO 94/16759 | 8/1994 |
| WO | WO 94/17369 | 8/1994 |
| WO | WO 94/17370 | 8/1994 |
| WO | WO 94/27576 | 12/1994 |
| WO | WO 94/27653 | 12/1994 |
| WO | WO 95/31182 | 11/1995 |
| WO | WO 96/00069 | 1/1996 |
| WO | WO 96/00070 | 1/1996 |
| WO | WO 96/00071 | 1/1996 |
| WO | WO 96/09846 | 4/1996 |
| WO | WO 96/10663 | 4/1996 |
| WO | WO 96/13161 | 5/1996 |
| WO | WO 96/13290 | 5/1996 |
| WO | WO 96/13291 | 5/1996 |
| WO | WO 96/13292 | 5/1996 |
| WO | WO 96/30068 | 10/1996 |
| WO | WO 96/31198 | 10/1996 |
| WO | WO 96/37198 | 11/1996 |
| WO | WO 97/16181 | 5/1997 |
| WO | WO 97/17948 | 5/1997 |
| WO | WO 97/23221 | 7/1997 |
| WO | WO 97/27804 | 8/1997 |
| WO | WO 97/31691 | 9/1997 |
| WO | WO 97/35562 | 10/1997 |
| WO | WO 97/36574 | 10/1997 |
| WO | WO 97/40819 | 11/1997 |
| WO | WO 97/49690 | 12/1997 |
| WO | WO 98/02186 | 1/1998 |
| WO | WO 98/16205 | 4/1998 |
| WO | WO 98/22170 | 5/1998 |
| WO | WO 98/29110 | 7/1998 |
| WO | WO 98/31346 | 7/1998 |
| WO | WO 98/34595 | 8/1998 |
| WO | WO 98/36651 | 8/1998 |
| WO | WO 98/37896 | 9/1998 |
| WO | WO 99/04797 | 2/1999 |
| WO | WO 99/16419 | 4/1999 |
| WO | WO 99/24433 | 5/1999 |
| WO | WO 99/37347 | 7/1999 |
| WO | WO 99/37625 | 7/1999 |
| WO | WO 99/44664 | 9/1999 |
| WO | WO 99/55362 | 11/1999 |
| WO | WO 99/59710 | 11/1999 |
| WO | WO 99/64094 | 12/1999 |
| WO | WO 00/00176 | 1/2000 |
| WO | WO 00/00215 | 1/2000 |
| WO | WO 00/00244 | 1/2000 |
| WO | WO 00/19991 | 4/2000 |
| WO | WO 00/27359 | 5/2000 |
| WO | WO 00/27363 | 5/2000 |
| WO | WO 00/28842 | 5/2000 |
| WO | WO 00/28979 | 5/2000 |
| WO | WO 00/29053 | 5/2000 |
| WO | WO 00/29167 | 5/2000 |
| WO | WO 00/35417 | 6/2000 |
| WO | WO 00/38618 | 7/2000 |
| WO | WO 00/44350 | 8/2000 |
| WO | WO 00/44730 | 8/2000 |
| WO | WO 00/47203 | 9/2000 |

| | | |
|---|---|---|
| WO | WO 00/51491 | 9/2000 |
| WO | WO 00/64940 | 11/2000 |
| WO | WO 00/66084 | 11/2000 |
| WO | WO 00/66106 | 11/2000 |
| WO | WO 00/66206 | 11/2000 |
| WO | WO 00/72827 | 12/2000 |
| WO | WO 00/76673 | 12/2000 |
| WO | WO 01/05459 | 1/2001 |
| WO | WO 01/17568 | 3/2001 |
| WO | WO 01/19528 | 3/2001 |
| WO | WO 01/29011 | 4/2001 |
| WO | WO 01/32144 | 5/2001 |
| WO | WO 01/41732 | 6/2001 |
| WO | WO 01/43801 | 6/2001 |
| WO | WO 01/95903 | 12/2001 |
| WO | WO 02/00198 | 1/2002 |
| WO | WO 02/24158 | 3/2002 |
| WO | WO 02/051466 | 7/2002 |
| WO | WO 02/056866 | 7/2002 |
| WO | WO 02/094234 | 11/2002 |
| WO | WO 02/098389 | 12/2002 |
| WO | WO 03/037412 | 5/2003 |

OTHER PUBLICATIONS

U.S. Appl. No. 11/964,630, filed Dec. 26, 2007, Hale et al.
U.S. Appl. No. 12/111,188, filed Apr. 28, 2008, Hale et al.
U.S. Appl. No. 12/117,737, filed May 8, 2008, Hale et al.
U.S. Appl. No. 12/211,247, filed Sep. 16, 2008, Sharma et al.
U.S. Appl. No. 12/211,554, filed Sep. 16, 2008, Sharma et al.
U.S. Appl. No. 12/211,628, filed Sep. 16, 2008, Lei et al.
U.S. Appl. No. 12/245,184, filed Oct. 3, 2008, Hale et al.
Office Action mailed Jan. 26, 2007 with respect to U.S. Appl. No. 10/057,198.
Office Action mailed Jul. 3, 2006 with respect to U.S. Appl. No. 10/057,198.
Office Action mailed Sep. 20, 2005 with respect to U.S. Appl. No. 10/057,198.
Office Action mailed Dec. 4, 2003 with respect to U.S. Appl. No. 10/057,198.
Office Action mailed Jan. 12, 2005 with respect to U.S. Appl. No. 10/057,197.
Office Action mailed Jun. 3, 2004 with respect to U.S. Appl. No. 10/057,197.
Office Action mailed Jun. 5, 2007 with respect to U.S. Appl. No. 10/057,197.
Office Action mailed Sep. 21, 2006 with respect to U.S. Appl. No. 10/057,197.
Office Action mailed Dec. 15, 2003 with respect to U.S. Appl. No. 10/057,197.
Office Action mailed Feb. 27, 2004 with respect to U.S. Appl. No. 10/146,080.
Office Action mailed Mar. 20, 2007 with respect to U.S. Appl. No. 10/146,080.
Office Action mailed Jun. 5, 2006 with respect to U.S. Appl. No. 10/146,080.
Office Action mailed Aug. 25, 2005 with respect to U.S. Appl. No. 10/146,080.
Office Action mailed Dec. 28, 2007 with respect to U.S. Appl. No, 10/146,080.
Office Action mailed Feb. 16, 2007 with respect to U.S. Appl. No. 10/146,088.
Office Action mailed Sep. 28, 2007 with respect to U.S. Appl. No. 10/146,088.
Office Action mailed Nov. 21, 2007 with respect to U.S. Appl. No. 10/146,088.
Office Action mailed Aug. 13, 2003 with respect to U.S. Appl. No. 10/153,313.
Office Action mailed Mar. 8, 2005 with respect to U.S. Appl. No. 10/718,982.
Anderson, M.E. (1982). "Recent Advances in Methodology and Concepts for Characterizing Inhalation Pharmacokinetic Parameters in Animals and Man," Drug Metabolism Reviews. 13(5):799-826.
Anonymous, (Jun. 1998) Guidance for Industry: Stability testing of drug substances and products, U.S. Department of Health and Human Services, FDA, CDER, CBER , pp. 1-110.
Bennett, R. L. et al. (1981). "Patient-Controlled Analgesia: A New Concept of Postoperative Pain Relief," Annual Surg, 195(6):700-705.
Benowitz (1994). "Individual Differences in Nicotine Kinetics and Metabolism in Humans," NIDA Research Monography, 2 pages.
BP: Chemicals Products-Barrier Resins (1999). located at <http://www.bp.com/chemicals/products/product.asp> (visited on Aug. 2, 2001), 8 pages.
Brand, P. et al. (Jun. 2000). "Total Deposition of Therapeutic Particles During Spontaneous and Controlled Inhalations," Journal of Pharmaceutical Sciences. 89(6):724-731.
Campbell, Fiona A. et al. (2001) "Are cannabinoids an effective and safe treatment option in the management of pain? A qualitative systemic review," BMJ, 323 pp. 1-6.
Carroll, M.E. et al. (1990), "Cocaine-Base Smoking in Rhesus Monkey: Reinforcing and Physiological Effects," Psychopharmacology (Berl) 102:443-450.
Cichewicz, Diana L. et al. (May 1999) "Enhancement of mu opioid antinociception by oral DELTA 9—tetrahydrocannabinol: Dose response analysis and receptor identification" Journal of Pharmacology and Experimental Therapeutics vol. 289 (2): 859-867.
Clark, A. and Byron, P. (1986). "Dependence of Pulmonary Absorption Kinetics on Aerosol Particle Size," Z. Erkrank. 166:13-24.
Dallas, C. et al. (1983). "A Small Animal Model for Direct Respiratory and Hemodynamic Measurements in Toxicokinetic Studies of Volatile Chemicals," Devlopments in the Science and Practice of Toxicology. Hayes, A. W. et al. eds., Elsevier Science Publishers, New York. pp. 419-422.
Darquenne, C. et al. (1997). "Aerosol Dispersion in Human Lung: Comparison Between Numerical Simulations and Experiments for Bolus Tests," American Physiological Society. 966-974.
Database Biosis "Online!" Biosciences Information Service, Philadelphia, PA 1979, Knight, V. et al., "Amantadine aerosol in humans", database accession No. PREV 198069035552 abstract, & Antimicrobial Agents and Chemotherapy 16(5):572-578.
Database Biosis "Online!" Biosciences Information Service, Philadelphia, PA 1979, Wilson. S.Z. et al., "Amatadine Aerosol Particle A.erosol Generation and Delivery to Man" Database accession No. PREV198069008137, abstract & Proceedings of the Society for Experimental Biology and Medicine 161(3):350-354.
Database WPI, Section CH, Week 198941, Derwent Publications Ltd., London, GB; AN 1989-297792 AP002230849 & JP 01 221313 (Nippon Create 1(K), Sep. 4, 1989, abstract.
Davies, C. N. et al. (May 1972). "Breathing of Half-Micron Aerosols," Journal of Applied Physiology. 32(5):591-600.
Dershwitz, M., M.D., et al. (Sep. 2000). "Pharmacokinetics and Pharmacodynamics of Inhaled versus Intravenous Morphine in Healthy Volunteers," Anesthesiology. 93(3): 619-628.
Drugs Approved by the FDA—Drug Name: Nicotrol Inhaler (2000) located at <http://www.centerwatch.com/patient/drugs/dru202.html> (Visited on Aug. 2, 2001), 2 pages.
Feynman, R.P. et al. (1964). "Chapter 32: Refractive Index of Dense Materials" The Feyman Lectures on Physics: Mainly Electromagnetism and Matter. Addison-Wesley: Publishing Company, Inc., Reading, Massachusetts: pp. 32-1-32-13.
Finlay, W. H. (2001). "The Mechanics of Inhaled Pharmaceutical Aerosols", Academic Press: San Diego Formula 2.39, pp. 3-14 (Table of Contents). pp. v-viii.
Gonda, I. (1991). "Particle Deposition in the Human Respiratory Tract,"Chapter 176, The Lung: Scientific Foundations. Crystal R.G. and West, J.B. (eds.), Raven Publishers, New York. pp. 2289-2294.
Graves, D. A. et al. (1983). "Patient-Controlled Analgesia" Annals of Internal Medicine. 99:360-366.
Hatsukami D., et al. (May 1990) "A Method for Delivery of Precise Doses of Smoked Cocaine-Base to Human." Pharmacology Biochemistry & Behavior. 36(1):1-7.
Heyder, J. et al. (1986). "Deposition of Particles in the Human Respiratory Tract in the Size Range 0.005-15 μm," J. Aerosol Sci. 17(5):811-822.

Huizer, H. (1987). "Analytical Studies on Illicit Heron. V. Efficacy of Volitization During Heroin Smoking." Pharmaceutisch Weekblad Scientific Edition. 9(4):203-211.

Hurt, R. D., MD and Robertson, C. R., PhD, (Oct. 1998). "Prying Open the Door to the Tobacco Industry's Secrets About Nicotine: The Minnesota Tobacco Trial," JAMA 280(13):1173-1181.

Hwang, S. L. (Jun. 1999). "Artificial Nicotine Studied: R. J. Reynolds Seeks to Develop Drugs that Mimic Tobacco's Potent Effects on Brain," Wall Street Journal, 3 pages.

James, A.C. et al., (1991). "The Respiratory Tract Deposition Model Proposed by the ICRP Task Group," Radiation Protection Dosimetry, 38(1/3):159-165.

Kim, M. H. and Patel, D.V. (1994). "'BOP' As a Reagent for Mild and Efficient Preparation of Esters," Tet. Letters 35:5603-5606.

Lichtman, A. H. et al. (1996). "Inhalation Exposure to Volatilized Opioids Produces Antinociception in Mice," Journal of Pharmacology and Experimental Therapeutics. 279(1):69-76 XP-001118649.

Lichtman, A. H. et al. (2000). "Pharmacological Evaluation of Aerosolized Cannabinoids in Mice" European Journal of Pharmacology, vol. 399, No. 2-3: 141-149.

Lopez, K. (Jul. 1999). "UK Researcher Develops Nicotinic Drugs with R. J. Reynolds," located at <http://www.eurekalert.org/pub_releases/1999-07/UoKM-Urdn-260799.php> (visited on Oct. 1, 2002), 1 page.

Martin, B. R. and Lue, L. P. (May/Jun. 1989). "Pyrolysis and Volatilization of Cocaine," Journal of Analytical Toxicology 13:158-162.

Mattox, A.J. and Carroll, M.E. (1996). "Smoked Heroin Self-Administration in Rhesus Monkeys," Psychopharmacology 125:195-201.

McCormick, A.S.M., et al., "Bronchospasm During Inhalation of Nebulized Midazolam," British Journal of Anesthesia, vol. 80 (4), Apr. 1988, pp. 564-565 XP001119488.

Meng, Y. et al. (1997). "Inhalation Studies with Drugs of Abuse", NIDA Research Monogragh 173:201-224.

Meng, Y., et al. (1999). "Pharmacological effects of methamphetamine and other stimulants via inhalation exposure," Drug and Alcohol Dependence. 53:111-120.

Pankow, J. (Mar. 2000). ACS Conference—San Francisco—Mar. 26, 2000. Chemistry of Tobacco Smoke. pp. 1-8.

Pankow, J. F. et al. (1997). "Conversion of Nicotine in Tobacco Smoke to Its Volatile and Available Free-Base Form through the Action of Gaseous Ammonia," Environ. Sci. Technol. 31:2428-2433.

Poochikian, G. and Bertha, C.M. (2000). "Inhalation Drug Product Excipient Controls: Significance and Pitfalls," Resp. Drug Deliv. VII: 109-115.

ScienceDaily Magazine, (Jul. 1999). "University of Kentucky Researcher Develops Nicotinic Drugs with R. J. Reynolds," located at <http://www.sciencedaily.com/releases/1999/07/990728073542.htm.> (visited on Sep. 23, 2002), 2 pages.

Seeman, J. et al. (1999). "The Form of Nicotine in Tobacco. Thermal Transfer of Nicotine and Nicotine Acid Salts to Nicotine in the Gas Phase," J. Agric. Food Chem. 47(12):5133-5145.

Sekine, H. and Nakahara, Y. (1987). "Abuse of Smoking Methamphetamine Mixed with Tobacco: 1. Inhalation Efficiency and Pyrolysis Products of Methamphetamine," Journal of Forensic Science 32(5):1271-1280.

Streitwieser, A. and Heathcock, C. H. eds., (1981). Introduction to Organic Chemistry. Second edition, Macmillan Publishing Co., Inc., New York, pp. ix-xvi. (Table of Contents).

Tsantilis, S. et al. (2001). "Sintering Time for Silica Particle Growth," Aerosol Science and Technology 34:237-246.

*Vapotronics, Inc.* (1998) located at http://www.vapotronics.com.au/banner.htm., 11 pages, (visited on Jun. 5, 2000).

Vaughan, N.P. (1990), "The Generation of Monodisperse Fibres of Caffeine" J. Aerosol Sci. 21(3): 453-462.

Ward, M. E. MD, et al. (Dec. 1997). "Morphine Pharmacokinetics after Pulmonary Administration from a Novel Aerosol Delivery System," Clinical Pharmocology & Therapeutics 62(6):596-609.

Williams, S. (Feb. 1999). "Rhone-Poulenc Rorer Inc. and Targacept Inc. Announce Alliance to Develop New Drugs to Treat Alzheimer's and Parkinson's Diseases" located at http://www.rpr.rpna.com/ABOUT_RPR/pressrels/1999/990209-targa.html (last visited on Jan. 28, 2000) 1 page.

Wood, R.W. et al. (1996). "Methylecgonidine Coats the Crack Particle." Pharmacology Biochemistry & Behavior. 53(1):57-66.

Wood, R.W. et al. (1996). "Generation of Stable Test Atmospheres of Cocaine Base and Its Pyrolyzate, Methylecgonidine, and Demonstration of Their Biological Activity." Pharmacology Biochemistry & Behavior. 55(2):237-248.

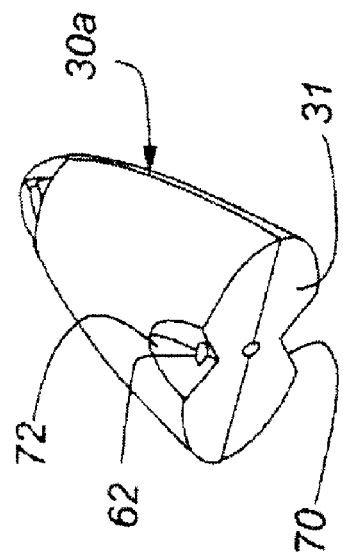
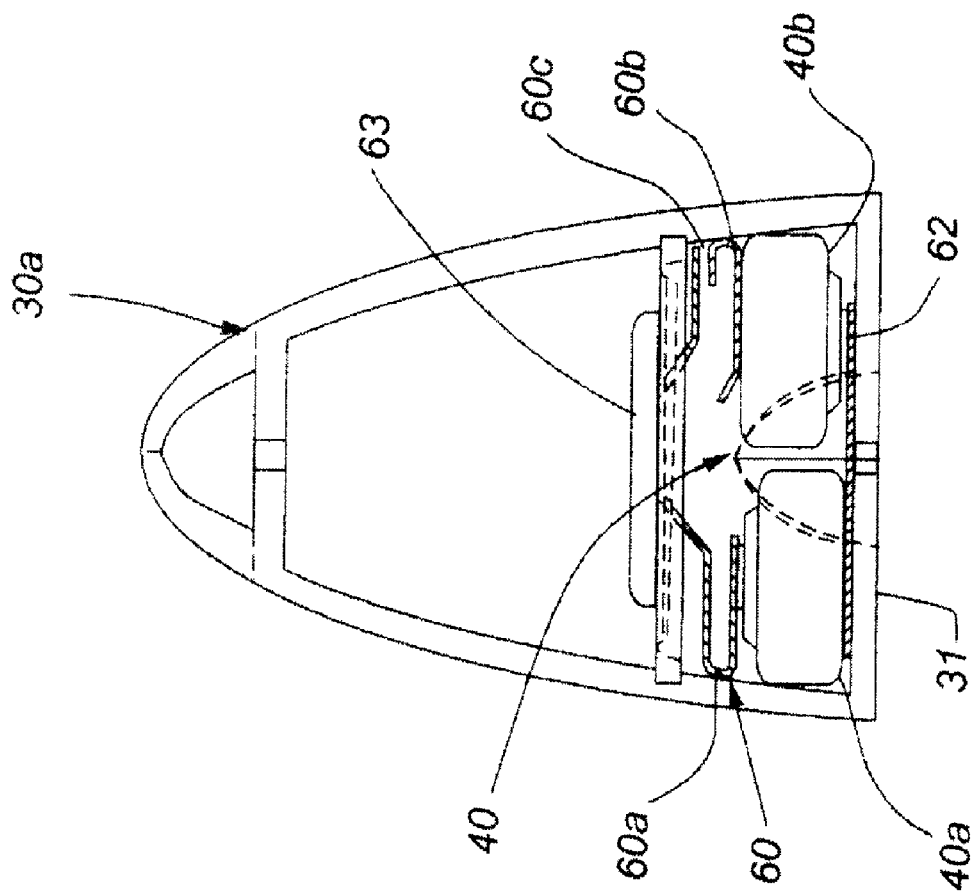

```
┌─────────────────────────────────────┐
│        PROVIDE SUBSTRATE            │ 310
└─────────────────────────────────────┘
                  │
                  ▼
┌─────────────────────────────────────┐
│ COAT DRUG ONTO EXTERIOR SURFACE OF SUBSTRATE │ 312
└─────────────────────────────────────┘
                  │
                  ▼
┌─────────────────────────────────────┐
│ PLACE SEALED BULBS CONTAINING COMBUSTIBLE │ 314
│ FILAMENTS AT INTERIOR OF SUBSTRATE  │
└─────────────────────────────────────┘
                  │
                  ▼
┌─────────────────────────────────────┐
│ IGNITE COMBUSTIBLE FILAMENT TO HEAT SUBSTRATE │ 316
│           AND VAPORIZE DRUG         │
└─────────────────────────────────────┘
                  │
                  ▼
┌─────────────────────────────────────┐
│   COOL VAPORIZED DRUG TO FORM AEROSOL │ 318
└─────────────────────────────────────┘
                  │
                  ▼
┌─────────────────────────────────────┐
│        INHALE AEROSOLIZED DRUG      │ 320
└─────────────────────────────────────┘
                                         300

Fig. 6
```

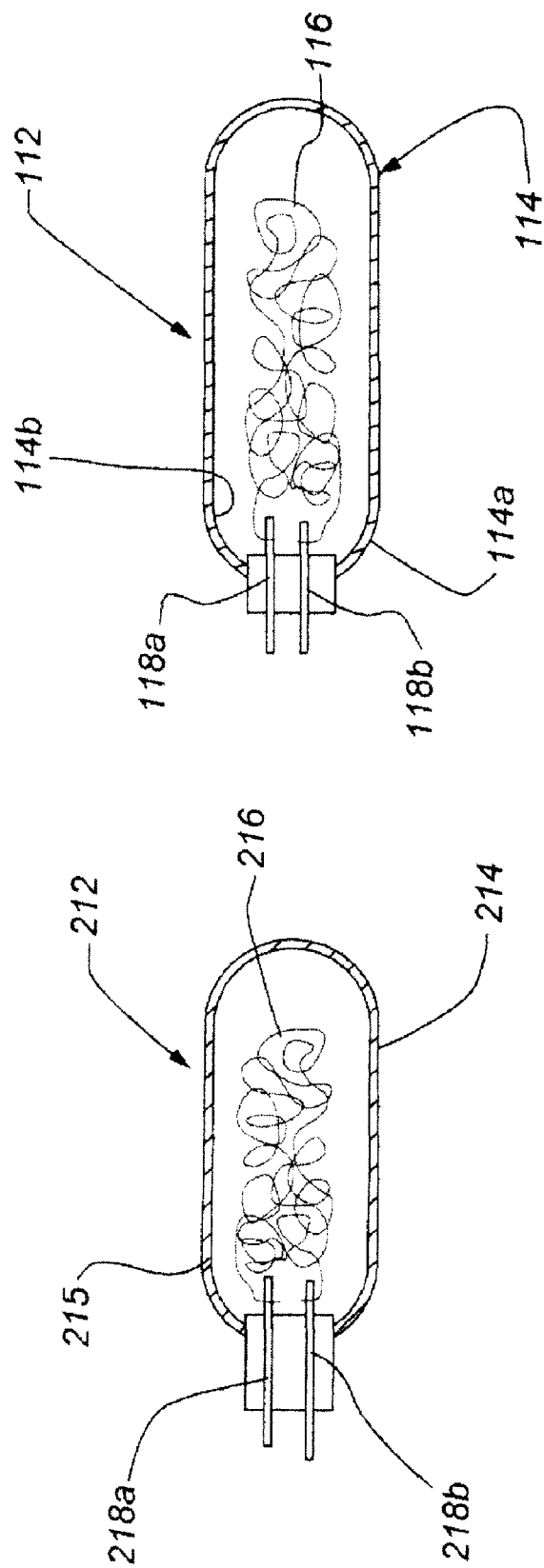

METHOD AND APPARATUS FOR VAPORIZING A COMPOUND

RELATED APPLICATIONS

This application is a continuation application of U.S. application Ser. No. 10/146,086, filed May 13, 2002, entitled "Method And Apparatus For Vaporizing A Compound", which is incorporated by reference herein in its entirety for any purpose.

FIELD OF THE INVENTION

This invention relates to methods and devices for delivery of an aerosol through an inhalation route. Specifically, the present invention relates a method and device for producing aerosols containing active drugs that are used in inhalation therapy.

BACKGROUND

It is known to aerosolize a drug for delivery by inhalation. For example, U.S. Pat. No. 5,099,861 to Clearman et al. for an Aerosol Delivery Article ("Clearman et al.") discloses a device including a substrate carrying a flavor or a drug. The substrate is heated by burning a fuel element which can be an "extruded carbonaceous material". Heating the substrate causes the flavor or drug to aerosolize which allows the user to inhale the flavor or drug. However, because the device disclosed in Clearman et al. burns a carbonaceous material to generate heat, heating and aerosol generation can be relatively slow. Additionally, the user must use a separate implement, such as a lighter or match, to ignite the fuel element. Also, the fuel element may generate undesirable products such as odor and smoke which may irritate the user or bystanders. These drawbacks to the Clearman et al. device can make the device relatively inconvenient.

U.S. Pat. No. 4,693,868 to Katsuda at al. for a Thermal Fumigator for Drugs ("Katsuda et al.") also discloses a device which can be used to vaporize a drug for inhalation delivery. As Clearman et al., Katsuda et al. also uses heat to vaporize the drug. However Katsuda et al. discloses ignition of a volatile fuel such as alcohol, petroleum or ether to generate the heat required to cause vaporization of a drug. The volatile fuel held by a container and is ignited by a metal catalyst included with the device. However, while combustion of the fuels disclosed in Katsuda is typically much more rapid than the combustion of the carbonaceous material fuel disclosed in Clearman et al., ignition of the fuels disclosed in Katsuda et al. can still be relatively slow. Additionally, the fuels disclosed in Katsuda et al. generate gaseous products upon combustion. Thus, if the fuel is contained in a sealed container, the pressure in the container may increase and cause a rupture. Additionally, even if a valve is provided for escape of the excess gas upon combustion, the escaping gas may generate an unpleasant odor.

SUMMARY OF THE INVENTION

The present invention includes a method and apparatus for providing inhalation delivery of a drug from a self contained unit. A method and device of the present invention allows rapid heating of a coated drug to produce a vapor. The rapid heating is followed by cooling and condensation of the vapor to provide an aerosol, also referred to as a condensation aerosol, which can be inhaled by a user to deliver a dose of the drug. The method and apparatus of the present invention achieves such rapid heating by using a sealed fuel cell having a combustible element. Because the fuel cell is sealed, there are advantageously no unpleasant combustion products released into the surrounding atmosphere. Additionally, the combustion of the element is relatively rapid and preferably does not generate gaseous products which would cause an increase in pressure in the sealed fuel cell.

A device for rapid heating of a coated substance in accordance with the present invention preferably includes a substrate which has an interior surface surrounding an interior region and an exterior surface upon which the coated substance is to be adhered. Though the substrate is preferably metallic, it does not need to be. A combustible element is placed in the interior region of the substrate and an igniter is connected to the combustible element. The igniter is for initiating oxidation of the combustible element. Preferably, the coated substance includes a drug to be vaporized inside of a housing to allow the vaporized drug to be inhaled by a user.

BRIEF DESCRIPTION OF THE DRAWINGS

FIG. 2 is a top view showing internal detail of a distal portion of the device shown in FIG. 1.

FIG. 3 is a perspective view showing the external surface of the distal portion of the device shown in FIG. 1.

FIG. 6 is a flow chart illustrating a method of delivering a drug via inhalation in accordance with the present invention.

FIG. 7 is a side view of an alternate embodiment of the sealed fuel cell and substrate useable with the housing illustrated in FIG. 1 in accordance with the present invention.

FIG. 8 is a side view of an alternate embodiment of the sealed fuel cell and substrate useable with the housing illustrated in FIG. 1 in accordance with the present invention.

DETAILED DESCRIPTION OF THE PREFERRED EMBODIMENTS

As used herein, the term "Aerosol" refers to a suspension of solid or liquid particles in a gas and the term "Vapor" refers to a gas, and "vapor phase" refers to a gas phase. The term "thermal vapor" refers to a vapor phase, aerosol, or mixture of aerosol-vapor phases, formed preferably by heating.

Figure 1:
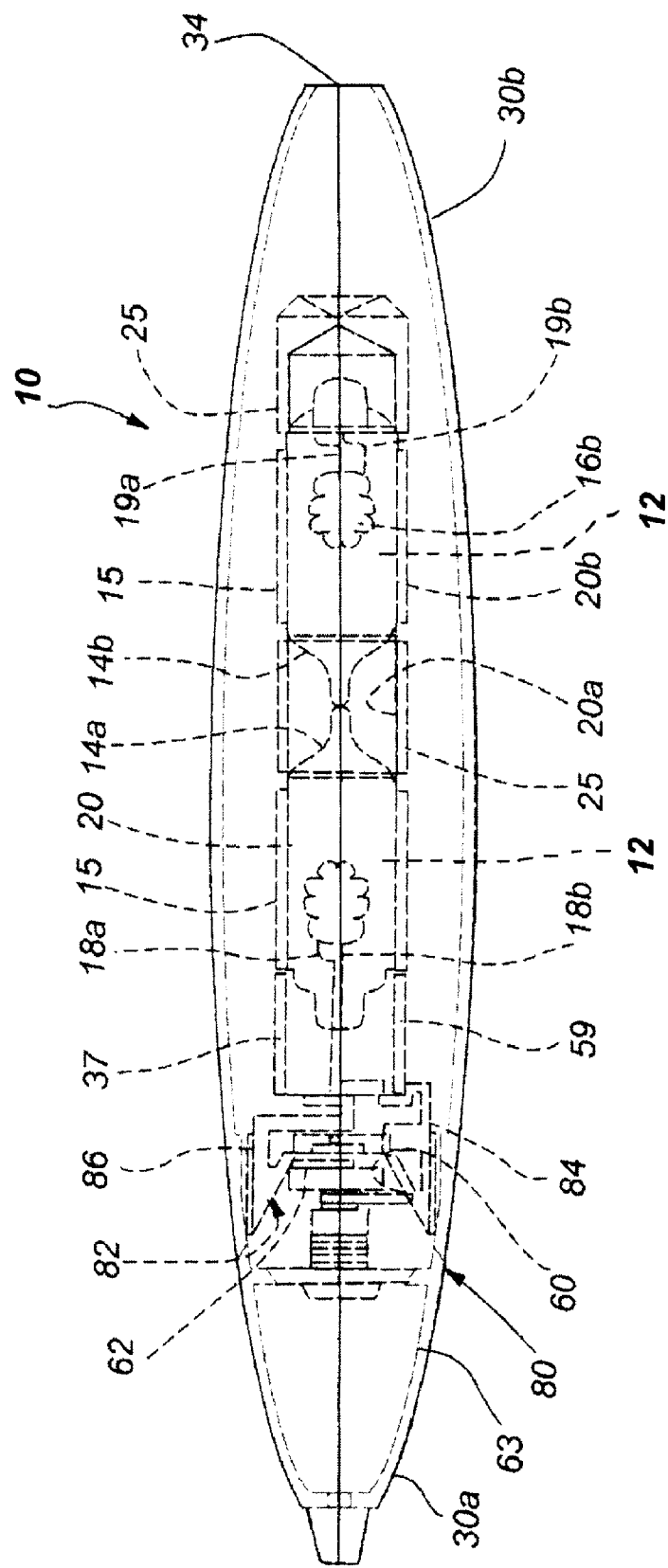
FIG. 1 is a side view showing internal detail of a device for vaporizing a drug including a sealed fuel cell in accordance with the present invention.

FIG. 1 is a side view showing internal construction of a preferred embodiment of a drug delivery device 10 that rapidly heats a drug using an exothermic reaction in accordance with the present invention. Drug delivery device 10 includes a fuel cell 12 for containing an exothermic reaction surrounded by a substrate 20 which is to be coated with a drug 15 or compound containing a drug. In the embodiment shown in FIG. 1, fuel cell 12 and substrate 20 are surrounded by a housing 30 having a distal end section 30a, a proximal end section 30b and including an airway 32 and mouthpiece 34. Airway 32 provides a path for aerosolized drug from the central region of housing 30 to mouthpiece 34, which facilitates inhalation of the aerosolized drug. Preferably, drug delivery device 10 includes two sections; a proximal end section 30b and a distal end section 30a which can be separated from each other along a division 90 as will be discussed in greater detail below.

In the embodiment shown in FIG. 1, fuel cell 12 includes two sealed bulbs 14a and 14b containing combustible elements 16a and 16b, respectively. Though FIG. 1 shows two bulbs 14a and 14b, it is also considered to include only a single bulb containing a single combustible element in fuel cell 12. Fuel cell 12 can essentially include standard flashbulbs, or a single standard flashbulb, of the type used for still photography. Preferably, the atmosphere inside each bulb 14a, 14b may contain a relatively high percentage of oxygen; preferably from 60% to 100% oxygen and more preferably from 75% to 95% oxygen. Preferably the pressure inside bulbs 14a and 14b is greater than atmospheric pressure and more preferably the pressure is between 5 and 10 atmospheres. Bulbs 14a and 14b are preferably formed from glass and may, but need not, be coated on an exterior surface with a polymer (not shown in FIG. 1) to contain glass particles if the glass shatters upon ignition of fuel cell 12. Such polymer coatings can include, without limitation, various laquers, cellulose-acetate, polyamides or Teflon®. Preferably, the thickness of such polymer coatings is between 0.01 mm and 1.0 mm. Bulbs suitable for use in a method and apparatus of the present invention have been available for several decades as articles of commerce manufactured by major bulb suppliers such as Osram Sylvania of Danvers, Mass. (under the brand name Blue Dot® flash bulbs), General Electric and Philips Corporation. Formation of a polymer coating useful for a glass bulb such as bulbs 14a and 14b is understood in the art and disclosed, for example, in U.S. Pat. No. 4,198,200 to Fonda et al. for Damage-Preventive Coatings which is hereby incorporated by reference in its entirety.

Combustible elements 16a and 16b are contained within sealed bulbs 14a and 14b, respectively. Preferably, combustible elements 16a and 16b include filaments formed from combustible metal such as aluminum, magnesium or zirconium formed into "wool" strands as is understood by those skilled in the art. However, combustible elements 16a and 16b could be formed from any combustible filament such as, without limitation, polymer filaments impregnated with combustible metal.

In the embodiment shown in FIG. 1, combustible element 16a is exposed to a set of metal electrodes 18a and 18b, across which a primer-coated resistive element is connected and which protrude through bulb 14a and are connected to an ignition power source 40 as described below. Electrodes 18a and 18b are preferably formed from copper but can be formed from any electrically conductive material such as, without limitation, aluminum. Power source 40 is preferably a relatively small, portable power source such as, without limitation a dry cell battery. If a dry cell battery is used as power source 40, the voltage of the battery is preferably between 1.5 and 9 volts. Electrodes 18a and 18b are connected to power source 40 through conductive lines 21a and 21b as described below.

As can be seen in FIG. 2, which is a top view of the distal end section 30a of housing 30 showing the interior construction, power source 40 preferably includes two 1.5 volt dry cell batteries 40a and 40b. It is to be understood that other types of power sources may be used with a drug delivery device in accordance with the present invention including, without limitation, a standard 9v battery. Batteries 40a and 40b are preferably connected in series via electrodes 60 and 62. Electrode 62 is preferably a substantially flat plate that is positioned between a base 31 of distal section 30a of housing 30 and batteries 40a and 40b. Electrode 60 preferably includes a moving section 60a in contact with battery 40a and separated by a gap 60c from a static section 60b, which is in contact with battery 40b. Moving section 60a and static section 60b are each formed into a hook shape and manufactured from an elastic conductive material such that section 60a can be elastically deformed to close gap 60c between moving section 60a and static section 60b to close a series circuit including batteries 40a and 40b.

FIG. 3 is a perspective view of the exterior of distal end section 30a of housing 30. As shown, distal end section 30a includes a upper notch 72 adjacent to base 31 and a lower notch 70, opposite upper notch 72 and also adjacent to base 31. As shown in FIGS. 1 and/or 3, electrode 62 extends through housing 30 at upper notch 72 on distal end section 30a of housing 30 and electrode 60 extends through housing 30 at lower notch 70.

Figure 5:
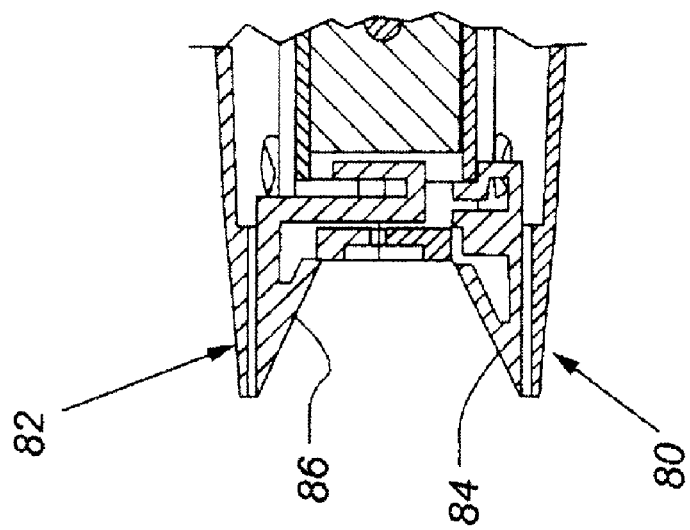
FIG. 5 is a detail side sectional view of the device shown in FIG. 1.

As shown in FIG. 5, which is a sectional side view of drug delivery device 10 showing detail near a portion of device 10 where it separates into two sections, housing 30 includes an upper fin portion 82 and a lower fin portion 80 which interconnect with upper notch 72 and lower notch 70, respectively, as shown on FIG. 3. Upper fin portion 82 includes a connecting electrode 86 which contacts electrode 62 when distal end portion 30a is engaged with proximal end portion 30b. Additionally, lower fin portion 80 includes a connecting electrode 84 which contacts electrode 60 when distal end portion 30a is engaged with proximal end portion 30b. Electrode 18a is preferably connected to electrode 62 through connecting electrode 86 and electrode 18b is preferably connected to electrode 60 through connecting electrode 84. Referring again to FIG. 2, in the embodiment shown, device 10 includes a button 63 in contact with a flattened portion of moving section 60a of electrode 60. Button 63 can be depressed by a user to close the circuit including batteries 40a and 40b and provide power to electrodes 60 and 62, respectively. In another embodiment of a fuel cell, the combustible element can be ignited by a piezoelectric crystal (or phosphor) which is in turn caused to discharge (or ignited by) a mechanical striker.

Referring again to FIG. 1, as noted above, the atmosphere inside sealed bulbs 14a and 14b preferably includes a high percentage of oxygen. Thus, if combustible elements 16a and 16b include a combustible metal such as magnesium or zirconium, providing a voltage from power source 40, causes the combustible element 16a to ignite and rapidly oxidize. The heat and light given off by the combustion of combustible element 16a causes sympathetic ignition of combustible element 16b. The exothermic combustion of elements 16a and 16b gives up heat to the surrounding atmosphere and to substrate 20. Preferably, each combustible element 16a, 16b is made up of approximately 1 mMole of metallic wool. Using this amount of wool, the exothermic reaction typically takes from 20 to 30 milliseconds. The heat provided by the exothermic reaction to substrate 20 causes vaporization of the drug coated onto substrate 20. As noted above, because the combustion of combustible elements 16a and 16b takes place in sealed bulbs 14a and 14b, respectively, no unpleasant combustion products escape into the surrounding atmosphere. Additionally, oxidation of a metal, such as occurs in combustion of combustible elements 16a and 16b, does not create gaseous products. As such, the pressure inside bulbs 14a and 14b does not increase excessively beyond that increase caused by the temperature rise after oxidation of combustible elements 16a and 16b has occurred.

Substrate 20 is preferably formed as a substantially cylindrical sheath having an opening in one end of the cylinder to allow insertion of bulbs 14a and 14b. The opposite end of the cylindrical sheath is preferably closed but may also be open. The cylindrical sheath forming substrate 20 is preferably tightly fit around bulbs 14a and 14b. Preferably, substrate 20 is machined from a rod of aluminum to form a cylinder of between approximately 0.05 mm and approximately 0.15 mm thickness. Substrate 20 may also be extruded, stamped or may be formed in any manner including rolling a sheet of aluminum or using aluminum foil and may be any suitable thickness. As shown in FIG. 1, substrate 20 can be formed with one or more increased thickness sections 25 to increase the rigidity of substrate 20. If used, increased thickness sections 25 are preferably located at areas of substrate 20 that do not contact bulbs 14a and 14b. To securely fit bulbs 14a and 14b inside substrate 20, substrate 20 can be slightly heated to expand the diameter of the cylinder. Bulbs 14a and 14b can then be positioned inside substrate 20 which will fit snugly around bulbs 14a and 14b upon cooling. Preferably, bulbs 14a and 14b are approximately 1cm in diameter. As such, the inner diameter of substrate 20 is also close to 1 cm.

Substrate 20 is supported at the interior of housing 30 in a cylindrical sleeve 37 which encloses substrate 20 along a fraction of the length thereof. Sleeve 37 is preferably formed unitarily with housing 30 and attaches to housing 30 at a base (not shown on FIG. 1) of front proximal end section 30b of housing 30. Substrate 20 can be affixed into sleeve 37 using known adhesives or simply by friction fit. Sleeve 37 includes a socket 59 supporting ends of conductive lines 21a and 21b of FIG. 1 and in which a base of bulb 14a can be plugged to allow electrodes 18a and 18b to contact conducting lines 21a and 21b in a known manner. In this way, power from power source 40 can be provided to combustible element 16a via conductive lines 21a and 21b. The opposite end of substrate 20, the end nearest to mouthpiece 34, is preferably closed and includes an increased thickness section 25.

It is contemplated that substrate 20 can be formed in a variety of shapes. For example, the substrate could also be in the shape of a rectangular box. Preferably, the substrate provides a large surface to volume ratio (e.g., greater than 100 per meter) and a large surface to mass ratio (e.g., greater than 1 $cm^2$ per gram). Additionally, a number of different materials can be used to construct the substrate. Classes of such materials include, without limitation, metals, inorganic materials, and polymers. The following are examples of the material classes: aluminum, silver, gold, stainless steel, copper and tungsten; silica, glass, silicon and alumina; graphite, porous carbons, carbon yarns and carbon felts; polytetrafluoroethylene and polyethylene glycol. Combinations of materials and coated variants of materials can be used as well. Examples of silica, alumina and silicon based materials include amorphous silica S-5631 (Sigma, St. Louis, Mo.), BCR171 (an alumina of defined surface area greater than 2 $m^2/g$ from Aldrich, St. Louis, Mo.) and a silicon wafer as used in the semiconductor industry. Carbon yarns and felts are available from American Kynol, Inc., New York, N.Y. Chromatography resins such as octadecycl silane chemically bonded to porous silica are exemplary coated variants of silica.

As shown in FIG. 1, substrate 20 includes an interior surface 20a, which is preferably, though not necessarily, in contact with the exterior of bulbs 14a and 14b, and an exterior surface 20b. As noted above, heat given off during the ignition of combustible element 16 is absorbed by substrate 20 resulting in vaporization of a drug coated onto exterior surface 20b of substrate 20. To improve absorption of heat by substrate 20, the interior surface 20a of substrate 20 is preferably anodized or otherwise coated to create a relatively dark surface.

It is also contemplated that a substrate can be coated onto bulbs 14a and 14b. If bulbs 14a and 14b do not include a polymer coating, the substrate can be coated directly onto the glass surface of bulbs 14a and 14b using known evaporation or electroplating techniques. If bulbs 14a and 14b do include a polymer coating, the substrate can be coated onto the polymer coating using known evaporation or electroplating techniques. If the substrate is coated onto bulbs 14a and 14b, any of the above mentioned materials which are useable with known evaporation or electroplating techniques, such as, without limitation, aluminum or stainless steel, may be used to form the substrate.

It is also considered that substrate 20 shown in FIG. 1 be eliminated and the glass forming the bulb act as the substrate. In such an embodiment, the drug can be coated directly onto the glass of the bulb. FIG. 7 is a diagram illustrating an embodiment of a fuel cell 212 that includes a sealed glass bulb 214 directly coated with a drug 215. At the interior of glass bulb 214 is combustible element 216, which can be substantially the same as combustible element 16 shown in FIG. 1. Fuel cell 212 also includes electrodes 218a and 218b, which can be substantially the same as electrodes 18a and 18b shown in FIG. 1. Combustible element 216 is exposed to electrodes 218a and 218b such that if a voltage is place across electrodes 218a and 218b, combustible element 216 will ignite. If such an embodiment in used, the bulb is preferably manufactured relatively thicker than if a separate metallic substrate such as substrate 20 is used or if the bulb is coated with a polymer coating. Thus, glasses that are resistant to thermal shock, such as Pyrex®, may be used at a thickness that prevents shattering upon ignition of combustible elements 216. Drug 215 is preferably coated onto the exterior of bulb 216 as discussed below.

It is also within the ambit of the present invention that the drug is impregnated into a polymer substrate and the substrate coated directly onto the bulb. FIG. 8 is a diagram illustrating an embodiment of a fuel cell 112 that includes a capsule 114 which includes an inner glass bulb 114b surrounded by an outer polymer substrate 114a. At the interior of glass bulb 114b, combustible element 116, which can be substantially the same as one of combustible elements 16a and 16b shown in FIG. 1, is exposed to contacts 118a and 118b, which can be substantially the same as contact 18a and 18b shown in FIG. 1. Fuel cell 112 can be used in housing 30 shown in FIG. 1 in the same way fuel cell 12 is used therein except that substrate 20 is not necessary. Polymer substrate 114a is preferably impregnated with a drug prior to use. Preferably, a substrate such as polymer substrate 114a is between 0.01 mm and 1 mm thick. A drug can be impregnated into polymer substrate 114a by exposing substrate 114a to the drug. For example, fuel cell 112 can be soaked in a solution containing a drug and a solvent, or just containing a drug, for 1 or more hours. In such an embodiment, the substrate can be formed from polyamides or Teflon® or other heat stable polymers.

Figure 4:
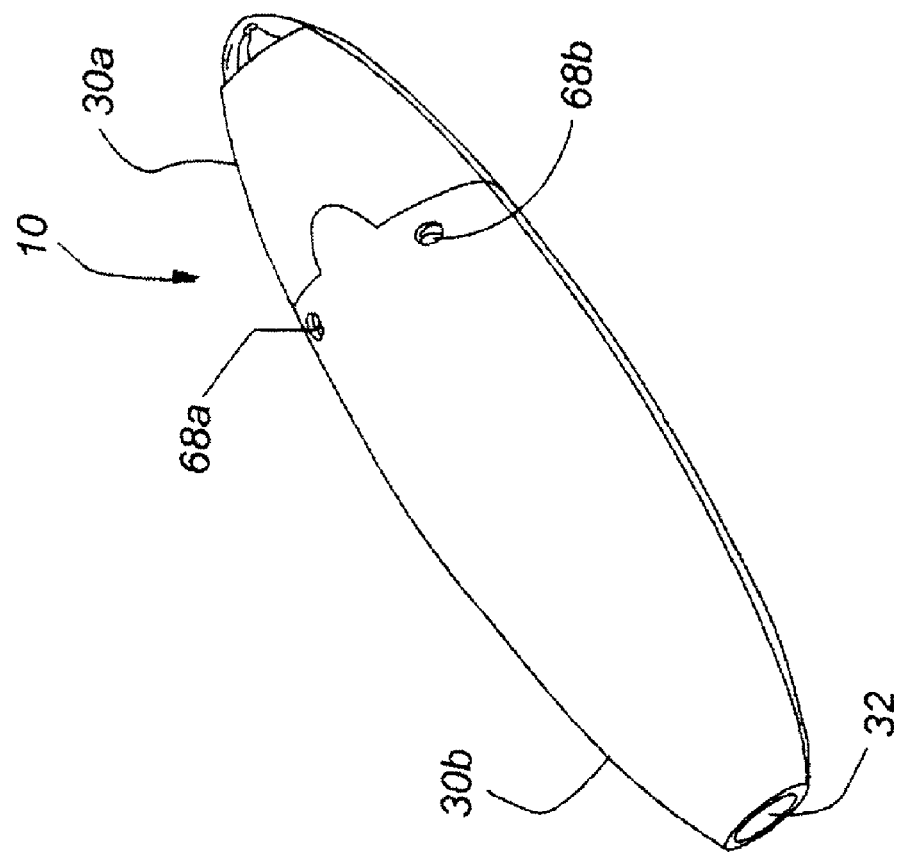
FIG. 4 is a perspective view showing the external surface of the device shown in FIG. 1.

FIG. 4 is a perspective view of drug delivery device 10 showing an exterior surface of housing 30 (as shown on FIG. 1). As shown, housing 30 is preferably ellipsoid in shape having an oval cross-section in a direction transverse to a long axis of device 10. As discussed above, substrate 20 and bulbs 14a and 14b are preferably rigidly connected to housing 30 so that substrate 20 and bulbs 14a and 14b are suspended in a substantially concentric manner inside housing 30. Proximal end section 30b of housing 30 preferably includes mouthpiece 34. Additionally, upper surface of housing 30 preferably includes openings 68a and 68b which, as shown in FIG. 1, are in fluid connection with airway 32 to allow air to pass from an exterior of housing 30 into airway 32. A lower surface of housing 30 preferably also contains openings, not visible in FIG. 4, opposite openings 68a and 68b. Housing 30 can be formed from various polymers including, without limitation, biodegradable polymers such as Biomax® available from E.I. du pont de Nemours and Company or other starch based polymers. Housing 30 can be formed by injection molding a top and bottom half and assembling the two halves as is well understood in the art. Preferably, but not necessarily, the oval cross-section of housing 30 transverse to the direction of the long axis of device 10 has an inner diameter of about 2 cm in a direction of a minor axis and about 3 cm in a direction of a major axis. It is also considered that housing 30 be formed in any other size or shape, such as, without limitation, a cylinder, rectangular box, triangular box or other shape.

As noted above, a proximal end section 30b of housing 30 is separable from a distal end section 30a of housing 30. As shown in FIG. 1 and discussed above, the distal end section 30a includes power supply 40 and an activation button 63 for drug delivery device 10. And, proximal end section 30b contains bulbs 14a, 14b, and substrate 20 coated with the drug to be delivered. Accordingly, proximal end section 30b can be detached from distal end section 30a upon consumption of the dosage included in proximal end section 30b and discarded. Distal end portion 30a, including power source 40, can then be re-used with another proximal end section containing a fresh dosage of coated drug. Distal end section 30a can advantageously be used a number of times in this way until power source 40 is depleted. Section 30a and 30b may, as is understood in the art, be molded to snap together, twist-lock or otherwise be joined together in preparation for aerosolization of the dosage form.

Aerosolization of a drug coated onto substrate 20 is accomplished by pressing button 63 to close the connection between power source 40 and combustible element 16a. Combustible element 16a ignites when a voltage from power source 40 is applied to it. As noted above, combustible element 16a is preferably a combustible metal that will rapidly oxidize in the atmosphere of fuel cell 12. To oxidize the amount of combustible metal preferably included in fuel cell 12 typically takes from 20 to 30 milliseconds and will release from about 800 joules to about 900 joules of energy. The release of this energy will cause the exterior surface 20b of substrate 20 to rise to a temperature of about 350 C to about 600 C. This is generally sufficient to cause the drug on exterior surface 20b of substrate 20 to vaporize. Preferably, the drug vapor then cools in airway 32 to form an aerosol. Preferably, the particle size range of the aerosolized drug is from about 1 μm to about 3 μm. To receive a dosage of the aerosolized drug, a user places mouthpiece 34 up to the user's mouth, activates by pressing the button 63, and inhales. Air will flow through openings of housing 30, through airway 32 and into mouthpiece 34 from which the aerosolized drug can enter the user's lungs.

FIG. 6 illustrates a method 300 of delivering a drug via inhalation in accordance with the present invention. In step 310 a substrate, such as substrate 20 shown in FIG. 1, is provided which can support a drug to be heated and vaporized as discussed above. The substrate is preferably formed to include an interior region and an exterior surface. In step 312, the drug is preferably coated onto an exterior surface of the substrate as discussed below. In step 314, at least one sealed bulb, such as bulb 14a shown in FIG. 1, is placed in the interior region of the substrate. As discussed above, the sealed bulb preferably contains a combustible filament including a combustible metal, such as aluminum, zirconium or magnesium. The combustible filament is preferably electrically connected to two electrodes that extend to the exterior of the bulb and which can be intermittently connected to a power supply, such as power supply 40 shown in FIG. 1, to allow for ignition of the combustible element. In step 316, the electrodes are switched into the power supply circuit and the combustible element is ignited. The ignition sets off an exothermic reaction which heats the substrate and vaporizes the drug coated thereon preferably as discussed above. In step 318, the drug is allowed to cool to form an aerosol. Preferably this cooling takes place in an airway, such as airway 32 shown in FIG. 1 surrounding the exterior surface of the substrate. In step 320, the aerosolized drug is inhaled by the user. In an alternate embodiment, in step 312, rather than coating a drug onto the exterior of the substrate provided in step 310, it is considered to impregnate the substrate with the drug to be aerosolized, as discussed above.

As noted above, the aerosol-forming device of the present invention rapidly heats a drug to produce a vapor, which is followed by cooling of the vapor and condensation of the vapor to provide an aerosol, also called a condensation aerosol. The drug composition is preferably heated in one of two forms: as pure active compound, or as a mixture of active compounds and pharmaceutically acceptable excipients.

The term "drug" as used herein means any chemical compound that is used in the prevention, diagnosis, treatment, or cure of disease, for the relief of pain, or to control or improve any physiological or pathological disorder in humans or animals. Classes of drugs include, without limitation, the following: antibiotics, anticonvulsants, antidepressants, antiemetics, antihistamines, antiparkinsonian drugs, antipsychotics, anxiolytics, drugs for erectile dysfunction, drugs for migraine headache, drugs for the treatment of alcoholism, muscle relaxants, nonsteroidal anti-inflammatories, opioids, other analgesics, stimulants and steroids.

Examples of antibiotics include cefmetazole, cefazolin, cephalexin, cefoxitin, cephacetrile, cephaloglycin, cephaloridine, cephalosporin c, cephalotin, cephamycin a, cephamycin b, cephamycin c, cepharin, cephradine, ampicillin, amoxicillin, hetacillin, carfecillin, carindacillin, carbenicillin, amylpenicillin, azidocillin, benzylpenicillin, clometocillin, cloxacillin, cyclacillin, methicillin, nafcillin, 2-pentenylpenicillin, penicillin n, penicillin o, penicillin s, penicillin v, chlorobutin penicillin, dicloxacillin, diphenicillin, heptylpenicillin, and metampicillin.

Examples of anticonvulsants include 4-amino-3-hydroxybutyric acid, ethanedisulfonate, gabapentin, and vigabatrin.

Examples of antidepressants include amitriptyline, amoxapine, benmoxine, butriptyline, clomipramine, desipramine, dosulepin, doxepin, imipramine, kitanserin, lofepramine, medifoxamine, mianserin, maprotoline, mirtazapine, nortriptyline, protriptyline, trimipramine, viloxazine, citalopram, cotinine, duloxetine, fluoxetine, fluvoxamine, milnacipran, nisoxetine, paroxetine, reboxetine, sertraline, tianeptine, acetaphenazine, binedaline, brofaromine, cericlamine, clovoxamine, iproniazid, isocarboxazid, moclobemide, phenyhydrazine, phenelzine, selegiline, sibutramine, tranylcypromine, ademetionine, adrafinil, amesergide, amisulpride, amperozide, benactyzine, bupropion, caroxazone, gepirone, idazoxan, metralindole, milnacipran, minaprine, nefazodone, nomifensine, ritanserin, roxindole, S-adenosylmethionine, tofenacin, trazodone, tryptophan, venlafaxine, and zalospirone.

Examples of antiemetics include alizapride, azasetron, benzquinamide, bromopride, buclizine, chlorpromazine, cinnarizine, clebopride, cyclizine, diphenhydramine, diphenidol, dolasetron methanesulfonate, droperidol, granisetron, hyoscine, lorazepam, metoclopramide, metopimazine, ondansetron, perphenazine, promethazine, prochlorperazine, scopolamine, triethylperazine, trifluoperazine, triflupromazine, trimethobenzamide, tropisetron, domeridone, and palonosetron.

Examples of antihistamines include azatadine, brompheniramine, chlorpheniramine, clemastine, cyproheptadine, dexmedetomidine, diphenhydramine, doxylamine, hydroxyzine, cetrizine, fexofenadine, loratidine, and promethazine.

Examples of antiparkinsonian drugs include amantadine, baclofen, biperiden, benztropine, orphenadrine, procyclidine, trihexyphenidyl, levodopa, carbidopa, selegiline, deprenyl, andropinirole, apomorphine, benserazide, bromocriptine, budipine, cabergoline, dihydroergokryptine, eliprodil, eptastigmine, ergoline, galanthamine, lazabemide, lisuride, mazindol, memantine, mofegiline, pergolide, pramipexole, propentofylline, rasagiline, remacemide, spheramine, terguride, entacapone, and tolcapone.

Examples of antipsychotics include acetophenazine, alizapride, amperozide, benperidol, benzquinamide, bromperidol, buramate, butaperazine, carphenazine, carpipramine, chlorpromazine, chlorprothixene, clocapramine, clomacran, clopenthixol, clospirazine, clothiapine, cyamemazine, droperidol, flupenthixol, fluphenazine, fluspirilene, haloperidol, mesoridazine, metofenazate, molindrone, penfluridol, pericyazine, perphenazine, pimozide, pipamerone, piperacetazine, pipotiazine, prochlorperazine, promazine, remoxipride, sertindole, spiperone, sulpiride, thioridazine, thiothixene, trifluperidol, triflupromazine, trifluoperazine, ziprasidone, zotepine, zuclopenthixol, amisulpride, butaclamol, clozapine, melperone, olanzapine, quetiapine, and risperidone.

Examples of anxiolytics include mecloqualone, medetomidine, metomidate, adinazolam, chlordiazepoxide, clobenzepam, flurazepam, lorazepam, loprazolam, midazolam, alpidem, alseroxlon, amphenidone, azacyclonol, bromisovalum, buspirone, calcium N-carboamoylaspartate, captodiamine, capuride, carbcloral, carbromal, chloral betaine, enciprazine, flesinoxan, ipsapiraone, lesopitron, loxapine, methaqualone, methprylon, propanolol, tandospirone, trazadone, zopiclone, and zolpidem.

Examples of drugs for erectile dysfunction include tadalafil (IC351), sildenafil, vardenafil, apomorphine, apomorphine diacetate, phentolamine, and yohimbine.

Examples of drugs for migraine headaches include almotriptan, alperopride, codeine, dihydroergotamine, ergotamine, eletriptan, frovatriptan, isometheptene, lidocaine, lisuride, metoclopramide, naratriptan, oxycodone, propoxyphene, rizatriptan, sumatriptan, tolfenamic acid, zolmitriptan, amitriptyline, atenolol, clonidine, cyproheptadine, diltiazem, doxepin, fluoxetine, lisinopril, methysergide, metoprolol, nadolol, nortriptyline, paroxetine, pizotifen, pizotyline, propanolol, protriptyline, sertraline, timolol, and verapamil.

Examples of drugs for the treatment of alcoholism include acamprosate, naloxone, naltrexone, and disulfiram.

Examples of muscle relaxants include baclofen, cyclobenzaprine, orphenadrine, quinine, and tizanidine.

Examples of nonsteroidal anti-inflammatories include aceclofenac, alclofenac, alminoprofen, amfenac, aminopropylon, amixetrine, aspirin, benoxaprofen, bermoprofen, bromfenac, bufexamac, butibufen, bucloxate, carprofen, choline, cinchophen, cinmetacin, clidanac, clopriac, clometacin, diclofenac, diflunisal, etodolac, fenclozate, fenoprofen, flutiazin, flurbiprofen, ibuprofen, ibufenac, indomethacin, indoprofen, ketoprofen, ketorolac, loxoprofen, mazipredone, meclofenamate, naproxen, oxaprozin, piroxicam, pirprofen, prodolic acid, salicylate, salsalate, sulindac, tofenamate, and tolmetin.

Examples of opioids include alfentanil, allylprodine, alphaprodine, anileridine, benzylmorphine, bezitramide, buprenorphine, butorphanol, carbiphene, cipramadol, clonitazene, codeine, dextromoramide, dextropropoxyphene, diamorphine, dihydrocodeine, diphenoxylate, dipipanone, fentanyl, hydromorphone, L-alpha acetyl methadol, lofentanil, levorphanol, meperidine, methadone, meptazinol, metopon, morphine, nalbuphine, nalorphine, oxycodone, papaveretum, pethidine, pentazocine, phenazocine, remifentanil, sufentanil, and tramadol.

Examples of other analgesics include apazone, benzpiperylon, benzydramine, bumadizon, clometacin, clonixin, ethoheptazine, flupirtine, nefopam, orphenadrine, propacetamol, and propoxyphene.

Examples of stimulants include amphetamine, brucine, dexfenfluramine, dextroamphetamine, ephedrine, fenfluramine, mazindol, methylphenidate, pemoline, phentermine, and sibutramine.

Examples of steroids include betamethasone, chloroprednisone, clocortolone, cortisone, desonide, dexamethasone, desoximetasone, difluprednate, estradiol, fludrocortisone, flumethasone, flunisolide, fluocortolone, fluprednisolone, hydrocortisone, meprednisone, methylprednisolone, paramethasone, prednisolone, prednisone, pregnan-3-alpha-ol-20-one, testosterone, and triamcinolone.

Pharmaceutically acceptable excipients may be volatile or nonvolatile. Volatile excipients, when heated, are concurrently volatilized, aerosolized and inhaled with the drug intended to be delivered. Classes of such excipients are known in the art and include, without limitation, gaseous, supercritical fluid, liquid and solid solvents. The following is a list of exemplary carriers within the classes: water; terpenes, such as menthol; alcohols, such as ethanol, propylene glycol, glycerol and other similar alcohols; dimethylformamide; dimethylacetamide; wax; and mixtures thereof.

Typically, the substrates of the present invention are coated with drug using a dip coating process. In such a process a solution of drug is first made. The solvent of the solution is chosen such that the drug is miscible in it at concentrations amenable to coating. Typical solvents for such a process include, but are not limited to, methylene chloride, ether, ethyl acetate and methanol. The substrate is dipped and removed from the solution at a constant rate. After dipping, solvent is allowed to evaporate and coated drug mass is calculated by subtracting the mass of the substrate from substrate plus compound. The dipping process can be repeated until the desired amount of drug is coated. Dip coaters suitable for use in implementing a method and/or apparatus of the present invention are commercially available. One such coater is the DC-2000, which can be obtained from Concoat Limited of Surry, England.

EXAMPLES

Example 1

Drug Aerosolization from a Polymer-Coated Flashbulb

A high power Sylvania® flashbulb, with its polymer coating intact, was weighed and placed in a vial of nicotine. Liquid nicotine was allowed to absorb into the polymer coating for one hour, and the excess liquid was removed by wiping with a tissue. The bulb was allowed to equilibrate overnight in a vial under an argon atmosphere. The vial was then opened and argon flowed over the bulb for 45 minutes. Re-weighing showed a total of 24.6 mg of nicotine was dissolved in the polymer coating. The bulb was enclosed in an 8 mL vial and fired by contact of its leads across the terminals of a AAA battery. A visible aerosol cloud was formed within the vial and allowed to re-condense on the walls. high performance liquid chromatography analysis of the condensate showed it to consist of 1.3 mg of pure nicotine.

Example 2

Drug Coated onto an Aluminum Substrate

A high-power flashcube (GE or Sylvania), which can produce 300-400 J of energy, was inserted into an anodized aluminum tube. The flashcube/tube assembly was dipped into an organic solution containing a drug and quickly removed. Evaporation of residual solvent from the assembly was performed by placing it into a vacuum chamber for 30 min. This left a film of drug coated on the exterior surface of the aluminum tube. The flashbulb assembly was electrically connected to two 1.5 V batteries and a switch using copper wires and then enclosed in a sealed, glass vial. Ignition of the flashbulb was performed by momentarily turning on the switch between the flashbulb and batteries. After ignition, the vial was kept closed for 30 minutes such that particles of volatilized drug coagulated and condensed on the inside surface of the vial. Analysis of the aerosol involved rinsing the vial with 5 mL of acetonitrile and injecting a sample of the organic solution into an high performance liquid chromatography device. Measurement with a fast thermocouple indicated that the aluminum tube heated up to 600° C. in 50 milliseconds. This translates into a heating rate of 12,000°/s.

One of ordinary skill in the art would understand that the experimental device detailed above could be transformed into an inhalation delivery device by excluding the sealed vial and including a housing to contain the assembly and electrical components. The housing would contain an air inlet and a mouthpiece such that, when drug volatilization occurred, an inhaled breath would carry the formed aerosol into the lungs of a subject.

The foregoing descriptions of specific embodiments of the present invention have been presented for purposes of illustration and description. They are not intended to be exhaustive or to limit the invention to the precise forms disclosed, and it should be understood that many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. Many other variations are also to be considered within the scope of the present invention.

What is claimed is:

1. A device for rapid heating of a composition comprising:
   a combustible filament contained within a sealed fuel cell for providing heat upon ignition;
   an igniter operatively associated with the combustible filament for igniting the combustible filament; and
   a composition comprising at least one drug in a heat exchange relationship with the combustible filament whereby upon ignition of the combustible filament the composition is vaporized.

2. The device of claim 1 further comprising a substrate having a surface in a heat exchange relationship with the combustible filament, the composition being coated on the substrate.

3. The device of claim 2, wherein the substrate is metallic.

4. The device of claim 3, wherein the metallic substrate comprises a sheath around the fuel cell.

5. The device of claim 2 wherein the substrate comprises an exterior surface of the fuel cell.

6. The device of claim 1 wherein the combustible filament comprises a combustible metal.

7. The device of claim 6 wherein the combustible metal is selected from the group consisting of magnesium, aluminum and zirconium.

8. The device of claim 1 wherein the combustible filament comprises zirconium.

9. A device for rapid heating of a composition comprising:
   a combustible filament contained within a sealed fuel cell having an exterior surface for providing heat upon ignition;
   an igniter operatively associated with the combustible filament for igniting the combustible filament; and
   a composition comprising at least one drug coated on the exterior surface of the fuel cell.

10. The device of claim 9 wherein the combustible filament comprises combustible metal.

11. The device of claim 10 wherein the combustible metal is selected from the group consisting of magnesium, aluminum and zirconium.

12. The device of claim 9 wherein the combustible filament comprises zirconium.

* * * * *